US010428135B2

(12) United States Patent
Fandl et al.

(10) Patent No.: US 10,428,135 B2
(45) Date of Patent: *Oct. 1, 2019

(54) FUSION POLYPEPTIDES CAPABLE OF ACTIVATING RECEPTORS

(71) Applicant: REGENERON PHARMACEUTICALS, INC., Tarrytown, NY (US)

(72) Inventors: James P. Fandl, LaGrangeville, NY (US); Gang Chen, Yorktown Heights, NY (US); Nicholas J. Papadopoulos, LaGrangeville, NY (US); Thomas H. Aldrich, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/808,749

(22) Filed: Nov. 9, 2017

(65) Prior Publication Data
US 2018/0162924 A1 Jun. 14, 2018

Related U.S. Application Data

(63) Continuation of application No. 14/511,786, filed on Oct. 10, 2014, now Pat. No. 9,842,549, which is a continuation of application No. 13/857,551, filed on Apr. 5, 2013, now Pat. No. 8,927,233, which is a continuation of application No. 13/628,082, filed on Sep. 27, 2012, now Pat. No. 8,470,324, which is a continuation of application No. 12/466,606, filed on May 15, 2009, now Pat. No. 8,298,532, which is a continuation-in-part of application No. 11/035,599, filed on Jan. 14, 2005, now Pat. No. 7,534,604.

(60) Provisional application No. 60/536,968, filed on Jan. 16, 2004.

(51) Int. Cl.
C07K 14/71 (2006.01)
C07H 21/04 (2006.01)
C07K 16/28 (2006.01)
C12P 21/02 (2006.01)

(52) U.S. Cl.
CPC ............ C07K 14/71 (2013.01); C07H 21/04 (2013.01); C07K 16/2863 (2013.01); C12P 21/02 (2013.01); C07K 2317/31 (2013.01); C07K 2317/52 (2013.01); C07K 2317/622 (2013.01); C07K 2317/75 (2013.01); C07K 2319/30 (2013.01)

(58) Field of Classification Search
None
See application file for complete search history.

(56) References Cited

U.S. PATENT DOCUMENTS

| | | | |
|---|---|---|---|
| 4,946,778 A | 6/1990 | Ladner et al. |
| 5,260,203 A | 11/1993 | Ladner et al. |
| 5,637,481 A | 6/1997 | Ledbetter et al. |
| 5,709,859 A | 1/1998 | Aruffo et al. |
| 5,747,033 A | 5/1998 | Davis et al. |
| 5,837,242 A | 11/1998 | Hollger et al. |
| 5,837,846 A | 11/1998 | Huston et al. |
| 5,864,019 A | 1/1999 | King et al. |
| 5,955,291 A | 9/1999 | Altalo et al. |
| 6,132,992 A | 10/2000 | Ledbetter et al. |
| 6,166,185 A | 12/2000 | Davis et al. |
| 6,204,023 B1 | 3/2001 | Robinson et al. |
| 6,285,564 B1 | 7/2001 | Davis et al. |
| 6,319,499 B1 | 11/2001 | Elliott |
| 6,433,143 B1 | 8/2002 | Davis et al. |
| 6,441,137 B1 | 8/2002 | Davis et al. |
| 6,492,123 B1 | 12/2002 | Hollger et al. |
| 6,627,415 B1 | 9/2003 | Davis et al. |
| 6,825,008 B2 | 11/2004 | Davis et al. |
| 6,846,914 B2 | 1/2005 | Valenzuela et al. |
| 6,881,395 B2 | 4/2005 | Valenzuela et al. |
| 6,892,019 B2 | 5/2005 | Nagayama et al. |
| 7,008,781 B1 | 3/2006 | Davis et al. |
| 7,045,302 B2 | 5/2006 | Davis et al. |
| 7,052,695 B2 | 5/2006 | Kalish et al. |
| 7,063,840 B2 | 6/2006 | Davis et al. |
| 7,083,950 B2 | 8/2006 | Stahl et al. |
| 7,534,604 B2 | 5/2009 | Fandl et al. |

(Continued)

FOREIGN PATENT DOCUMENTS

| | | |
|---|---|---|
| WO | WO 2001/090192 | 11/2001 |
| WO | WO 2003/092611 | 11/2003 |
| WO | WO 2005/070966 | 8/2005 |

OTHER PUBLICATIONS

Dietsch, M.T., et al., J. (1993) "Bispecific receptor globulins, novel tools for the study of cellular interactions." J. Immunol. Methods 162(1):123-132.

(Continued)

Primary Examiner — Marianne P Allen
(74) Attorney, Agent, or Firm — Eileen Woo; Alston & Bird LLP

(57) ABSTRACT

A fusion polypeptide comprising $(A)_x$-M-$(A')_y$, wherein A and A' are each polypeptides capable of binding a target receptor. The fusion polypeptides of the invention form multimeric proteins which activate the target receptor. A and A' may be each be an antibody or fragment derived from an antibody specific for a target receptor, such as the same or different scFv fragments, and/or a ligand or ligand fragment or derivative capable of binding the target protein, M is a multimerizing component, and X and Y are independently a number between 1-10.

27 Claims, No Drawings
Specification includes a Sequence Listing.

(56) References Cited

U.S. PATENT DOCUMENTS

| | | |
|---|---|---|
| 7,871,610 B2 | 1/2011 | Wood |
| 8,298,532 B2 | 10/2012 | Fandl et al. |
| 8,470,324 B2 | 6/2013 | Fandl et al. |
| 8,597,898 B2 | 12/2013 | Fandl |
| 8,865,430 B2 | 10/2014 | Fandl et al. |
| 8,927,233 B2 | 1/2015 | Fandl et al. |
| 9,840,549 B2 | 12/2017 | Fandl et al. |

OTHER PUBLICATIONS

Gerstmayer, B., et al. (1997) "Costirnulation of T-cell proliferation by a chimeric B7-antibody fusion protein." Cancer immunol. Immunother. 45(3-4):156-158.

Rohrbach, F., et al. (2000) "Construction and characterization of blspecffic costimulatory molecules containing a minimized CO86 (B7-2) domain and slngle•chaln antibody fragments for tumor targeting," Clinicial Cancer Res. (6 11):4314-4322.

Lu, D., et al. (1999) "Acquired antagonistic activity of a bispedfic dlabody directed against two different epitopea on vascular endothelial growth factor receptor 2." J. Immunol, Methods 230(1-2):159-171.

Rippmann, J.F., et al. (2000) "Fusion of the tissue factor extracel-luier domain to a tumour stroma specific single-chain fragment variable antibody results in an antigen-speclfic coagulation-promoting molecule." Blochem. J. 349(Pt.3):805-812.

Zuo, Z., et al. (2000) "An efficient route to the production of an IgG-like bispeolflo antibody." Protein Engineering 13 (6):361-367.

Pereboev, A.V., et al. (2002) "Coxsacklevirus-adenovirus receptor genetically fused to anti-human CD40 scFv enhances edenoviral transduction of dendritic cells." Gene Therapy 9(17)1189-1193.

Alt, M., et al. (1999) "Novel tetravalent and bispecific IgG-like antibody molecules combining single-chain diabodies with the immunoglobulln gammal Fc or CH3 region." FEBS Lett. 454(1-2):90-94.

Connelly, R.J., et al. (1998) "Mitogenic properties of a bispecific single-chain Fv-Ig fusion generated from CD2-specific mAb to distinct epitopes." Int. Immunol. 10(12):1863-1872.

Gerstmayer B,, et al. (1997) -Costimulation of T cell proliferation by a chimeric B7-2 antibody fusion protein specifically targeted to cells expressing the erbB2 protoroncogene, J. Immunol. 158(10):4584-90.

Hayden. M.S., et al. (1994) "Single-chain mono- and blspeclfic antibody derivatives with novel biological properties and antitumour activity from a COS cell transient expression system." Ther, Immunol, 1(1):3-15.

Neri, 0,, et al. (1995) High-affinity antigen binding by chelating recombinant antibodies (CRAbs). J. Mol. Bio. 246 (3):367-373.

Lu D., at al. (2001) "Complete Inhibition of vascular endothelial growth factor (VEGF) activities with a bifunctional diabody directed against both VEGF kinase receptors, frns-like tyrosine kinase receptor and kinase insert domain-containing receptor." Cancer Res. 61(19):7002-7008.

Davis, S., et al. (2003) "Angiopoletins have distinct modular domains essential for receptor binding, dimerization and supercluster-ing," Nature Struct, Blol, 10(1):38-44.

PCT/US2005/001246 International Search Report dated Oct. 10, 2005.

PCT/US2005/001246 International Preliminary Report of Patent-ability dated Jul. 17, 2006.

PCT/US2005/001246 Written Opinion of the International Search-ing authority dated Jul. 17, 2006.

U.S. Appl. No. 11/035,599 Final Office Action dated Dec. 13, 2007.

U.S. Appl. No. 11/035,599 Notice of Allowance dated Jan. 9, 2009.

U.S. Appl. No. 11/035,599 Non-Final Office Action dated Jun. 3, 2008.

U.S. Appl. No. 12/466,606 Non-Final Office Action dated Apr. 6, 2012.

U.S. Appl. No. 12/466,606 Notice of Allowance dated Sep. 19, 2012.

U.S. Appl. No. 12/466,606 Non-Final Office Action dated Oct. 11, 2012.

U.S. Appl. No. 12/466,606 Restriction Requirement dated Sep. 17, 2010.

U.S. Appl. No. 13/020,875 Non-Final Office Action dated Dec. 29, 2011.

U.S. Appl. No. 13/628,082 Notice of Allowance dated Mar. 7, 2013.

U.S. Appl. No. 13/628,084 Final Office Action dated Jul. 24, 2013.

U.S. Appl. No. 13/628,084 Notice of Allowance dated Oct. 1, 2013.

U.S. Appl. No. 13/628,084 Non-Final Office Action dated Mar. 4, 2013.

U.S. Appl. No. 13/857,551 Final Office Action dated Feb. 21, 2014.

U.S. Appl. No. 13/857,551 Notice of Allowance dated Sep. 15, 2014.

U.S. Appl. No. 13/857,551 Non-Final Office Action dated Dec. 6, 2013.

U.S. Appl. No. 13/892,630 Notice of Allowance dated Aug. 14, 2014.

U.S. Appl. No. 13/892,630 Restriction Requirement dated Dec. 6, 2013.

U.S. Appl. No. 11/035,599 Non-Final Office Action dated Jun. 19, 2007.

U.S. Appl. No. 12/466,606 Final Office Action dated Mar. 22, 2011.

U.S. Appl. No. 12/466,606 Non-Final Office Action dated Dec. 2, 2010.

U.S. Appl. No. 13/857,551 Notice of Allowance dated May 7, 2014.

U.S. Appl. No. 13/892,630 Notice of Allowance dated Jul. 23, 2014.

Barton, et al., "Crystal structures of the Tie2 receptor ectodomain and the angiopoietin-2-Tie2 complex", Nature Structural & Molecu-lar Biology, vol. 13, No. 6, pp. 524-532 (Jun. 2006).

Saharinen, et al., "Multiple angiopoietin recombinant proteins acti-vate the Tie 1 receptor tyrosine kinase and promote its interaction with Tie2", *The Journal of Cell Biology*, Vo. 169, No. 2 pp. 239-243, (Apr. 25, 2005).

Yancopoulos, et al., "Vascular-specific growth factors and blood vessel formation", *Nature*, vol. 407, pp. 242-248, (Sep. 14, 2000).

Jendreyko, et al., "Protein Synthesis, Post-Translation Modification, and Degradation: Intradiabodies, Bispecific, Tetravalent Antibodies for the Simultaneous Functional Knockout of Two Cell Surface Receptors", *J. Biol. Chem.*, 278:47812-47819 (2003).

U.S. Appl. No. 14/511,786 Restriction Requirement dated Jun. 25, 2015.

U.S. Appl. No. 14/511,786 Non-Final Office Action dated Sep. 22, 2015.

U.S. Appl. No. 14/511,786 Final Office Action dated Apr. 29, 2016.

U.S. Appl. No. 14/511,786 Non-Final Office Action dated Sep. 27, 2016.

U.S. Appl. No. 14/511,786 Final Office Action dated Apr. 13, 2017.

U.S. Appl. No. 14/511,786 Notice of Allowance dated Aug. 16, 2017.

SEQUENCE LISTING

<160> NUMBER OF SEQ ID NOS: 53

<210> SEQ ID NO 1
<211> LENGTH: 32
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: 18
<223> OTHER INFORMATION: n = a, t, c or g

<400> SEQUENCE: 1
cttccggaat tcsargtnma gctgsagsag tc                    32

<210> SEQ ID NO 2
<211> LENGTH: 35
<212> TYPE: DNA
<213> ORGANISM: Artificial Sequence
<220> FEATURE:

```
<223> OTHER INFORMATION: Primers
<220> FEATURE:
<221> NAME/KEY: misc_feature
<222> LOCATION: 18
<223> OTHER INFORMATION: n = a, t, c or g

<400> SEQUENCE: 2
cttccggaat tcsargtnma gctgsagsag tcwgg                               35

<210> SEQ ID NO 3
<211> LENGTH: 34
<212> TYPE: DNA
<213> ORGANISM: Artificial Sequence
<220> FEATURE:
<223> OTHER INFORMATION: Primers

<400> SEQUENCE: 3
cttccggaat tccaggttac tctgaaagwg tstg                                34

<210> SEQ ID NO 4
<211> LENGTH: 32
<212> TYPE: DNA
<213> ORGANISM: Artificial Sequence
<220> FEATURE:
<223> OTHER INFORMATION: Primers

<400> SEQUENCE: 4
cttccggaat tcgaggtcca rctgcaacar tc                                  32

<210> SEQ ID NO 5
<211> LENGTH: 32
<212> TYPE: DNA
<213> ORGANISM: Artificial Sequence
<220> FEATURE:
<223> OTHER INFORMATION: Primers

<400> SEQUENCE: 5
cttccggaat tccaggtcca actvcagcar cc                                  32

<210> SEQ ID NO 6
<211> LENGTH: 32
<212> TYPE: DNA
<213> ORGANISM: Artificial Sequence
<220> FEATURE:
<223> OTHER INFORMATION: Primers

<400> SEQUENCE: 6
cttccggaat tcgaggtgaa sstggtggaa tc                                  32

<210> SEQ ID NO 7
<211> LENGTH: 32
<212> TYPE: DNA
<213> ORGANISM: Artificial Sequence
<220> FEATURE:
<223> OTHER INFORMATION: Primers

<400> SEQUENCE: 7
cttccggaat tcgatgtgaa cttggaagtg tc                                  32

<210> SEQ ID NO 8
<211> LENGTH: 36
<212> TYPE: DNA
<213> ORGANISM: Artificial Sequence
<220> FEATURE:
<223> OTHER INFORMATION: Primers

<400> SEQUENCE: 8
```
ggaagatcta tagacagatg ggggtgtcgt tttggc    36

<210> SEQ ID NO 9
<211> LENGTH: 32
<212> TYPE: DNA
<213> ORGANISM: Artificial Sequence
<220> FEATURE:
<223> OTHER INFORMATION: Primers

<400> SEQUENCE: 9
gggagctcga yattgtgmts acmcarwctm ca    32

<210> SEQ ID NO 10
<211> LENGTH: 30
<212> TYPE: DNA
<213> ORGANISM: Artificial Sequence
<220> FEATURE:
<223> OTHER INFORMATION: Primers

<400> SEQUENCE: 10
ggtgcatgcg gatacagttg gtgcagcatc    30

<210> SEQ ID NO 11
<211> LENGTH: 39
<212> TYPE: DNA
<213> ORGANISM: Artificial Sequence
<220> FEATURE:
<223> OTHER INFORMATION: Primers

<400> SEQUENCE: 11
ggggatatcc accatggrat gsagctgkgt matsctctt    39

<210> SEQ ID NO 12
<211> LENGTH: 39
<212> TYPE: DNA
<213> ORGANISM: Artificial Sequence
<220> FEATURE:
<223> OTHER INFORMATION: Primers

<400> SEQUENCE: 12
ggggatatcc accatgract tcgggytgag ctkggtttt    39

<210> SEQ ID NO 13
<211> LENGTH: 38
<212> TYPE: DNA
<213> ORGANISM: Artificial Sequence
<220> FEATURE:
<223> OTHER INFORMATION: Primers

<400> SEQUENCE: 13
ggggatatcc accatggctg tcttggggct gctcttct    38

<210> SEQ ID NO 14
<211> LENGTH: 38
<212> TYPE: DNA
<213> ORGANISM: Artificial Sequence
<220> FEATURE:
<223> OTHER INFORMATION: Primers

<400> SEQUENCE: 14
ggggatatcc accatggaga cagacacact cctgctat    38

<210> SEQ ID NO 15
<211> LENGTH: 39
<212> TYPE: DNA

```
<213> ORGANISM: Artificial Sequence
<220> FEATURE:
<223> OTHER INFORMATION: Primers

<400> SEQUENCE: 15
ggggatatcc accatggatt ttcaggtgca gattttcag                                  39

<210> SEQ ID NO 16
<211> LENGTH: 40
<212> TYPE: DNA
<213> ORGANISM: Artificial Sequence
<220> FEATURE:
<223> OTHER INFORMATION: Primers

<400> SEQUENCE: 16
ggggatatcc accatgragt cacakacyca ggtcttyrta                                 40

<210> SEQ ID NO 17
<211> LENGTH: 40
<212> TYPE: DNA
<213> ORGANISM: Artificial Sequence
<220> FEATURE:
<223> OTHER INFORMATION: Primers

<400> SEQUENCE: 17
ggggatatcc accatgaggk ccccwgctca gytyctkggr                                 40

<210> SEQ ID NO 18
<211> LENGTH: 37
<212> TYPE: DNA
<213> ORGANISM: Artificial Sequence
<220> FEATURE:
<223> OTHER INFORMATION: Primers

<400> SEQUENCE: 18
ggggatatcc accatgaagt tgcttgttag gctgttg                                    37

<210> SEQ ID NO 19
<211> LENGTH: 54
<212> TYPE: DNA
<213> ORGANISM: Artificial Sequence
<220> FEATURE:
<223> OTHER INFORMATION: Primers

<400> SEQUENCE: 19
gactggtctc atgcaggcgc gcctcaggtt aagctggagg agtctggacc tggc                 54

<210> SEQ ID NO 20
<211> LENGTH: 75
<212> TYPE: DNA
<213> ORGANISM: Artificial Sequence
<220> FEATURE:
<223> OTHER INFORMATION: Primers

<400> SEQUENCE: 20
tgagccccct ccaccggacc ctccaccgcc cgatccaccg cccctgagg agacggtgac            60 tgaggttcct tgacc                                                            75

<210> SEQ ID NO 21
<211> LENGTH: 75
<212> TYPE: DNA
<213> ORGANISM: Artificial Sequence
<220> FEATURE:
<223> OTHER INFORMATION: Primers

<400> SEQUENCE: 21
```

```
gggggcggtg atcgggcgg tggagggtcc ggtggagggg gctcagatat tgtgatgacc    60
cagtctccaa aatcc                                                   75
```

<210> SEQ ID NO 22
<211> LENGTH: 54
<212> TYPE: DNA
<213> ORGANISM: Artificial Sequence
<220> FEATURE:
<223> OTHER INFORMATION: Primers

<400> SEQUENCE: 22

```
cgatgcggcc gctcagcccg ggccccgttt cagctccagc ttggtcccag cacc        54
```

<210> SEQ ID NO 23
<211> LENGTH: 43
<212> TYPE: DNA
<213> ORGANISM: Artificial Sequence
<220> FEATURE:
<223> OTHER INFORMATION: Primers

<400> SEQUENCE: 23

```
gatcggcgcg cctgaggtca agctgcagga gtctggagct gag                    43
```

<210> SEQ ID NO 24
<211> LENGTH: 75
<212> TYPE: DNA
<213> ORGANISM: Artificial Sequence
<220> FEATURE:
<223> OTHER INFORMATION: Primers

<400> SEQUENCE: 24

```
tgagccccct ccaccggacc ctccaccgcc cgatccaccg cccctgagg agactgtgag    60 agtggtgcct tggcc                                                   75
```

<210> SEQ ID NO 25
<211> LENGTH: 75
<212> TYPE: DNA
<213> ORGANISM: Artificial Sequence
<220> FEATURE:
<223> OTHER INFORMATION: Primers

<400> SEQUENCE: 25

```
gggggcggtg atcgggcgg tggagggtcc ggtggagggg gctcagatat tgtgctgaca    60
cagtctccag cttcc                                                   75
```

<210> SEQ ID NO 26
<211> LENGTH: 54
<212> TYPE: DNA
<213> ORGANISM: Artificial Sequence
<220> FEATURE:
<223> OTHER INFORMATION: Primers

<400> SEQUENCE: 26

```
cgatgcggcc gctcagcccg ggccccgttt gatttccagc ttggtgcctc cacc        54
```

<210> SEQ ID NO 27
<211> LENGTH: 29
<212> TYPE: PRT
<213> ORGANISM: Mus musculus

<400> SEQUENCE: 27

```
Met His Arg Pro Arg Arg Arg Gly Thr Arg Pro Pro Pro Leu Ala Leu
1               5                   10                  15
```

Leu Ala Ala Leu Leu Ala Ala Arg Gly Ala Asp Ala
            20                  25

<210> SEQ ID NO 28
<211> LENGTH: 762
<212> TYPE: PRT
<213> ORGANISM: Artificial Sequence
<220> FEATURE:
<223> OTHER INFORMATION: Synthetic

<400> SEQUENCE: 28

Met His Arg Pro Arg Arg Gly Thr Arg Pro Pro Leu Ala Leu
1               5                   10                  15

Leu Ala Ala Leu Leu Ala Ala Arg Gly Ala Asp Ala Gly Ala Pro
            20                  25                  30

Glu Val Lys Leu Gln Glu Ser Gly Ala Glu Leu Met Lys Pro Gly Ala
            35                  40                  45

Ser Val Lys Ile Ser Cys Lys Ala Thr Gly Tyr Thr Phe Ser Ser Tyr
        50                  55                  60

Trp Ile Glu Trp Val Lys Gln Arg Pro Gly His Gly Leu Glu Trp Ile
65                  70                  75                  80

Gly Glu Ile Leu Pro Gly Ser Gly Ser Thr Asn Tyr Asn Glu Lys Phe
                85                  90                  95

Lys Gly Lys Ala Thr Phe Thr Ala Asp Thr Phe Ser Asn Thr Ala Tyr
            100                 105                 110

Met Gln Leu Ser Ser Leu Thr Ser Glu Asp Ser Ala Val Tyr Tyr Cys
        115                 120                 125

Ala Arg Phe Asp Gly Tyr Leu Pro Phe Asp His Trp Gly Gln Gly Thr
    130                 135                 140

Thr Leu Thr Val Ser Ser Gly Gly Gly Ser Gly Gly Gly Gly Ser
145                 150                 155                 160

Gly Gly Gly Gly Ser Asp Ile Val Leu Thr Gln Ser Pro Ala Ser Leu
                165                 170                 175

Ala Val Ser Leu Gly Gln Arg Ala Thr Ile Ser Cys Arg Ala Ser Lys
            180                 185                 190

Ser Val Ile Thr Ser Gly Tyr Ser Tyr Met His Trp Tyr Gln Gln Lys
        195                 200                 205

Pro Gly Gln Pro Pro Gln Leu Leu Ile Tyr Leu Ala Ser Asn Leu Glu
    210                 215                 220

Ser Gly Val Pro Ala Arg Phe Ser Gly Ser Gly Ser Gly Thr Asp Phe
225                 230                 235                 240

Thr Leu Asn Ile His Pro Val Glu Glu Glu Asp Ala Ala Thr Tyr Tyr
                245                 250                 255

Cys His His Ser Arg Glu Leu Pro Arg Thr Phe Gly Gly Gly Thr Lys
            260                 265                 270

Leu Glu Ile Lys Arg Gly Pro Gly Asp Lys Thr His Thr Cys Pro Pro
        275                 280                 285

Cys Pro Ala Pro Glu Leu Leu Gly Gly Pro Ser Val Phe Leu Phe Pro
    290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
            340                 345                 350

```
Glu Glu Gln Tyr Asn Ser Thr Tyr Arg Val Ser Val Leu Thr Val
            355                 360                 365
Leu His Gln Asp Trp Leu Asn Gly Lys Glu Tyr Lys Cys Lys Val Ser
    370                 375                 380
Asn Lys Ala Leu Pro Ala Pro Ile Glu Lys Thr Ile Ser Lys Ala Lys
385                 390                 395                 400
Gly Gln Pro Arg Glu Pro Gln Val Tyr Thr Leu Pro Pro Ser Arg Asp
                405                 410                 415
Glu Leu Thr Lys Asn Gln Val Ser Leu Thr Cys Leu Val Lys Gly Phe
            420                 425                 430
Tyr Pro Ser Asp Ile Ala Val Glu Trp Glu Ser Asn Gly Gln Pro Glu
        435                 440                 445
Asn Asn Tyr Lys Thr Thr Pro Pro Val Leu Asp Ser Asp Gly Ser Phe
450                 455                 460
Phe Leu Tyr Ser Lys Leu Thr Val Asp Lys Ser Arg Trp Gln Gln Gly
465                 470                 475                 480
Asn Val Phe Ser Cys Ser Val Met His Glu Ala Leu His Asn His Tyr
                485                 490                 495
Thr Gln Lys Ser Leu Ser Leu Ser Pro Gly Lys Gly Gly Gly Gly Ser
            500                 505                 510
Gly Ala Pro Gln Val Lys Leu Glu Glu Ser Gly Pro Gly Leu Val Lys
        515                 520                 525
Pro Ser Gln Ser Leu Ser Leu Thr Cys Thr Val Thr Gly Tyr Ser Ile
    530                 535                 540
Thr Ser Asp Tyr Ala Trp Asn Trp Ile Arg Gln Phe Pro Gly Asn Lys
545                 550                 555                 560
Leu Glu Trp Met Gly Tyr Ile Asn Tyr Ser Gly Ile Thr Ser Tyr Asn
                565                 570                 575
Pro Ser Leu Lys Ser Arg Ile Ser Ile Thr Arg Asp Thr Ser Lys Asn
            580                 585                 590
Gln Phe Phe Leu Gln Leu Asn Ser Val Thr Ala Glu Asp Thr Ala Thr
        595                 600                 605
Tyr Tyr Cys Ala Arg Tyr Tyr Gly Ser Ser Tyr Asn Tyr Tyr Gly Met
    610                 615                 620
Asp Tyr Trp Gly Gln Gly Thr Ser Val Thr Val Ser Ser Gly Gly Gly
625                 630                 635                 640
Gly Ser Gly Gly Gly Gly Ser Gly Gly Gly Gly Ser Asp Ile Val Met
                645                 650                 655
Thr Gln Ser Pro Lys Ser Met Ser Met Ser Val Gly Glu Arg Val Thr
            660                 665                 670
Leu Asn Cys Lys Ala Ser Glu Asn Val Gly Thr Tyr Ile Ser Trp Tyr
        675                 680                 685
Gln Gln Lys Pro Asp Gln Ser Pro Lys Leu Leu Ile Tyr Gly Ala Ser
    690                 695                 700
Asn Arg Tyr Pro Gly Val Pro Asp Arg Phe Thr Gly Ser Gly Ser Ala
705                 710                 715                 720
Thr Asp Phe Thr Leu Thr Ile Ser Ser Leu Gln Ala Glu Asp Leu Ala
                725                 730                 735
Asp Tyr His Cys Gly Gln Gly Tyr Thr Tyr Leu Thr Phe Gly Ala Gly
            740                 745                 750
Thr Lys Leu Glu Leu Lys Arg Gly Pro Gly
        755                 760
```

<210> SEQ ID NO 29
<211> LENGTH: 761
<212> TYPE: PRT
<213> ORGANISM: Artificial Sequence
<220> FEATURE:
<223> OTHER INFORMATION: Synthetic

<400> SEQUENCE: 29

```
Met His Arg Pro Arg Arg Gly Thr Arg Pro Pro Leu Ala Leu
1               5                   10                  15

Leu Ala Ala Leu Leu Leu Ala Ala Arg Gly Ala Asp Ala Gly Ala Pro
            20                  25                  30

Gln Val Lys Leu Glu Glu Ser Gly Pro Gly Leu Val Lys Pro Ser Gln
            35                  40                  45

Ser Leu Ser Leu Thr Cys Thr Val Thr Gly Tyr Ser Ile Thr Ser Asp
    50                  55                  60

Tyr Ala Trp Asn Trp Ile Arg Gln Phe Pro Gly Asn Lys Leu Glu Trp
65                  70                  75                  80

Met Gly Tyr Ile Asn Tyr Ser Gly Ile Thr Ser Tyr Asn Pro Ser Leu
                85                  90                  95

Lys Ser Arg Ile Ser Ile Thr Arg Asp Thr Ser Lys Asn Gln Phe Phe
            100                 105                 110

Leu Gln Leu Asn Ser Val Thr Ala Glu Asp Thr Ala Thr Tyr Tyr Cys
        115                 120                 125

Ala Arg Tyr Tyr Gly Ser Ser Tyr Asn Tyr Tyr Gly Met Asp Tyr Trp
    130                 135                 140

Gly Gln Gly Thr Ser Val Thr Val Ser Ser Gly Gly Gly Gly Ser Gly
145                 150                 155                 160

Gly Gly Gly Ser Gly Gly Gly Ser Asp Ile Val Met Thr Gln Ser
                165                 170                 175

Pro Lys Ser Met Ser Met Ser Val Gly Glu Arg Val Thr Leu Asn Cys
            180                 185                 190

Lys Ala Ser Glu Asn Val Gly Thr Tyr Ile Ser Trp Tyr Gln Gln Lys
        195                 200                 205

Pro Asp Gln Ser Pro Lys Leu Leu Ile Tyr Gly Ala Ser Asn Arg Tyr
    210                 215                 220

Pro Gly Val Pro Asp Arg Phe Thr Gly Ser Gly Ser Ala Thr Asp Phe
225                 230                 235                 240

Thr Leu Thr Ile Ser Ser Leu Gln Ala Glu Asp Leu Ala Asp Tyr His
                245                 250                 255

Cys Gly Gln Gly Tyr Thr Tyr Leu Thr Phe Gly Ala Gly Thr Lys Leu
            260                 265                 270

Glu Leu Lys Arg Gly Pro Gly Asp Lys Thr His Thr Cys Pro Pro Cys
        275                 280                 285

Pro Ala Pro Glu Leu Leu Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365
```

-continued

```
His Gln Asp Trp Leu Asn Gly Lys Glu Tyr Lys Cys Lys Val Ser Asn
370                 375                 380
Lys Ala Leu Pro Ala Pro Ile Glu Lys Thr Ile Ser Lys Ala Lys Gly
385                 390                 395                 400
Gln Pro Arg Glu Pro Gln Val Tyr Thr Leu Pro Pro Ser Arg Asp Glu
            405                 410                 415
Leu Thr Lys Asn Gln Val Ser Leu Thr Cys Leu Val Lys Gly Phe Tyr
        420                 425                 430
Pro Ser Asp Ile Ala Val Glu Trp Glu Ser Asn Gly Gln Pro Glu Asn
    435                 440                 445
Asn Tyr Lys Thr Thr Pro Pro Val Leu Asp Ser Asp Gly Ser Phe Phe
450                 455                 460
Leu Tyr Ser Lys Leu Thr Val Asp Lys Ser Arg Trp Gln Gln Gly Asn
465                 470                 475                 480
Val Phe Ser Cys Ser Val Met His Glu Ala Leu His Asn His Tyr Thr
                485                 490                 495
Gln Lys Ser Leu Ser Leu Ser Pro Gly Lys Gly Gly Gly Gly Ser Gly
            500                 505                 510
Ala Pro Gln Val Lys Leu Glu Glu Ser Gly Pro Gly Leu Val Lys Pro
        515                 520                 525
Ser Gln Ser Leu Ser Leu Thr Cys Thr Val Thr Gly Tyr Ser Ile Thr
    530                 535                 540
Ser Asp Tyr Ala Trp Asn Trp Ile Arg Gln Phe Pro Gly Asn Lys Leu
545                 550                 555                 560
Glu Trp Met Gly Tyr Ile Asn Tyr Ser Gly Ile Thr Ser Tyr Asn Pro
                565                 570                 575
Ser Leu Lys Ser Arg Ile Ser Ile Thr Arg Asp Thr Ser Lys Asn Gln
            580                 585                 590
Phe Phe Leu Gln Leu Asn Ser Val Thr Ala Glu Asp Thr Ala Thr Tyr
        595                 600                 605
Tyr Cys Ala Arg Tyr Tyr Gly Ser Ser Tyr Asn Tyr Tyr Gly Met Asp
    610                 615                 620
Tyr Trp Gly Gln Gly Thr Ser Val Thr Val Ser Ser Gly Gly Gly Gly
625                 630                 635                 640
Ser Gly Gly Gly Gly Ser Gly Gly Gly Gly Ser Asp Ile Val Met Thr
                645                 650                 655
Gln Ser Pro Lys Ser Met Ser Met Ser Val Gly Glu Arg Val Thr Leu
            660                 665                 670
Asn Cys Lys Ala Ser Glu Asn Val Gly Thr Tyr Ile Ser Trp Tyr Gln
        675                 680                 685
Gln Lys Pro Asp Gln Ser Pro Lys Leu Leu Ile Tyr Gly Ala Ser Asn
    690                 695                 700
Arg Tyr Pro Gly Val Pro Asp Arg Phe Thr Gly Ser Gly Ser Ala Thr
705                 710                 715                 720
Asp Phe Thr Leu Thr Ile Ser Ser Leu Gln Ala Glu Asp Leu Ala Asp
                725                 730                 735
Tyr His Cys Gly Gln Gly Tyr Thr Tyr Leu Thr Phe Gly Ala Gly Thr
            740                 745                 750
Lys Leu Glu Leu Lys Arg Gly Pro Gly
            755                 760

<210> SEQ ID NO 30
<211> LENGTH: 730
<212> TYPE: PRT
```

<213> ORGANISM: Artificial Sequence
<220> FEATURE:
<223> OTHER INFORMATION: Synthetic

<400> SEQUENCE: 30

```
Met His Arg Pro Arg Arg Gly Thr Arg Pro Pro Leu Ala Leu
1               5                   10                  15

Leu Ala Ala Leu Leu Leu Ala Ala Arg Gly Ala Asp Ala Gly Ala Pro
                20                  25                  30

Gln Val Lys Leu Glu Glu Ser Gly Pro Gly Leu Val Lys Pro Ser Gln
            35                  40                  45

Ser Leu Ser Leu Thr Cys Thr Val Thr Gly Tyr Ser Ile Thr Ser Asp
    50                  55                  60

Tyr Ala Trp Asn Trp Ile Arg Gln Phe Pro Gly Asn Lys Leu Glu Trp
65                  70                  75                  80

Met Gly Tyr Ile Asn Tyr Ser Gly Ile Thr Ser Tyr Asn Pro Ser Leu
                85                  90                  95

Lys Ser Arg Ile Ser Ile Thr Arg Asp Thr Ser Lys Asn Gln Phe Phe
            100                 105                 110

Leu Gln Leu Asn Ser Val Thr Ala Glu Asp Thr Ala Thr Tyr Tyr Cys
        115                 120                 125

Ala Arg Tyr Tyr Gly Ser Ser Tyr Asn Tyr Tyr Gly Met Asp Tyr Trp
    130                 135                 140

Gly Gln Gly Thr Ser Val Thr Val Ser Ser Gly Gly Gly Gly Ser Gly
145                 150                 155                 160

Gly Gly Gly Ser Gly Gly Gly Ser Asp Ile Val Met Thr Gln Ser
                165                 170                 175

Pro Lys Ser Met Ser Met Ser Val Gly Glu Arg Val Thr Leu Asn Cys
                180                 185                 190

Lys Ala Ser Glu Asn Val Gly Thr Tyr Ile Ser Trp Tyr Gln Gln Lys
            195                 200                 205

Pro Asp Gln Ser Pro Lys Leu Leu Ile Tyr Gly Ala Ser Asn Arg Tyr
    210                 215                 220

Pro Gly Val Pro Asp Arg Phe Thr Gly Ser Gly Ser Ala Thr Asp Phe
225                 230                 235                 240

Thr Leu Thr Ile Ser Ser Leu Gln Ala Glu Asp Leu Ala Asp Tyr His
                245                 250                 255

Cys Gly Gln Gly Tyr Thr Tyr Leu Thr Phe Gly Ala Gly Thr Lys Leu
                260                 265                 270

Glu Leu Lys Arg Gly Pro Gly Asp Lys Thr His Thr Cys Pro Pro Cys
        275                 280                 285

Pro Ala Pro Glu Leu Leu Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
```

```
                385                 390                 395                 400
        Gln Pro Arg Glu Pro Gln Val Tyr Thr Leu Pro Pro Ser Arg Asp Glu
                        405                 410                 415

Leu Thr Lys Asn Gln Val Ser Leu Thr Cys Leu Val Lys Gly Phe Tyr
                    420                 425                 430

Pro Ser Asp Ile Ala Val Glu Trp Glu Ser Asn Gly Gln Pro Glu Asn
                        435                 440                 445

Asn Tyr Lys Thr Thr Pro Pro Val Leu Asp Ser Asp Gly Ser Phe Phe
                450                 455                 460

Leu Tyr Ser Lys Leu Thr Val Asp Lys Ser Arg Trp Gln Gln Gly Asn
        465                 470                 475                 480

Val Phe Ser Cys Ser Val Met His Glu Ala Leu His Asn His Tyr Thr
                        485                 490                 495

Gln Lys Ser Leu Ser Leu Ser Pro Gly Lys Gly Gly Gly Gly Ser Gly
                    500                 505                 510

Ala Pro Phe Arg Asp Cys Ala Asp Val Tyr Gln Ala Gly Phe Asn Lys
                        515                 520                 525

Ser Gly Ile Tyr Thr Ile Tyr Ile Asn Asn Met Pro Glu Pro Lys Lys
                530                 535                 540

Val Phe Cys Asn Met Asp Val Asn Gly Gly Gly Trp Thr Val Ile Gln
        545                 550                 555                 560

His Arg Glu Asp Gly Ser Leu Asp Phe Gln Arg Gly Trp Lys Glu Tyr
                        565                 570                 575

Lys Met Gly Phe Gly Asn Pro Ser Gly Glu Tyr Trp Leu Gly Asn Glu
                    580                 585                 590

Phe Ile Phe Ala Ile Thr Ser Gln Arg Gln Tyr Met Leu Arg Ile Glu
                        595                 600                 605

Leu Met Asp Trp Glu Gly Asn Arg Ala Tyr Ser Gln Tyr Asp Arg Phe
                610                 615                 620

His Ile Gly Asn Glu Lys Gln Asn Tyr Arg Leu Tyr Leu Lys Gly His
        625                 630                 635                 640

Thr Gly Thr Ala Gly Lys Gln Ser Ser Leu Ile Leu His Gly Ala Asp
                        645                 650                 655

Phe Ser Thr Lys Asp Ala Asp Asn Asp Asn Cys Met Cys Lys Cys Ala
                    660                 665                 670

Leu Met Leu Thr Gly Gly Trp Trp Phe Asp Ala Cys Gly Pro Ser Asn
                        675                 680                 685

Leu Asn Gly Met Phe Tyr Thr Ala Gly Gln Asn His Gly Lys Leu Asn
                690                 695                 700

Gly Ile Lys Trp His Tyr Phe Lys Gly Pro Ser Tyr Ser Leu Arg Ser
        705                 710                 715                 720

Thr Thr Met Met Ile Arg Pro Leu Asp Phe
                        725                 730

<210> SEQ ID NO 31
<211> LENGTH: 730
<212> TYPE: PRT
<213> ORGANISM: Artificial Sequence
<220> FEATURE:
<223> OTHER INFORMATION: Synthetic

<400> SEQUENCE: 31

Met His Arg Pro Arg Arg Gly Thr Arg Pro Pro Leu Ala Leu
1               5                   10                  15

Leu Ala Ala Leu Leu Leu Ala Ala Arg Gly Ala Asp Ala Gly Ala Pro
```

-continued

```
            20                  25                  30
Gln Val Lys Leu Glu Glu Ser Gly Pro Gly Leu Val Lys Pro Ser Gln
            35                  40                  45

Ser Leu Ser Leu Thr Cys Thr Val Thr Gly Tyr Ser Ile Thr Ser Asp
     50                  55                  60

Tyr Ala Trp Asn Trp Ile Arg Gln Phe Pro Gly Asn Lys Leu Glu Trp
 65                  70                  75                  80

Met Gly Tyr Ile Asn Tyr Ser Gly Ile Thr Ser Tyr Asn Pro Ser Leu
                 85                  90                  95

Lys Ser Arg Ile Ser Ile Thr Arg Asp Thr Ser Lys Asn Gln Phe Phe
            100                 105                 110

Leu Gln Leu Asn Ser Val Thr Ala Glu Asp Thr Ala Thr Tyr Tyr Cys
            115                 120                 125

Ala Arg Tyr Tyr Gly Ser Ser Tyr Asn Tyr Tyr Gly Met Asp Tyr Trp
        130                 135                 140

Gly Gln Gly Thr Ser Val Thr Val Ser Ser Gly Gly Gly Gly Ser Gly
145                 150                 155                 160

Gly Gly Gly Ser Gly Gly Gly Ser Asp Ile Val Met Thr Gln Ser
                165                 170                 175

Pro Lys Ser Met Ser Met Ser Val Gly Glu Arg Val Thr Leu Asn Cys
                180                 185                 190

Lys Ala Ser Glu Asn Val Gly Thr Tyr Ile Ser Trp Tyr Gln Gln Lys
            195                 200                 205

Pro Asp Gln Ser Pro Lys Leu Leu Ile Tyr Gly Ala Ser Asn Arg Tyr
            210                 215                 220

Pro Gly Val Pro Asp Arg Phe Thr Gly Ser Gly Ser Ala Thr Asp Phe
225                 230                 235                 240

Thr Leu Thr Ile Ser Ser Leu Gln Ala Glu Asp Leu Ala Asp Tyr His
                245                 250                 255

Cys Gly Gln Gly Tyr Thr Tyr Leu Thr Phe Gly Ala Gly Thr Lys Leu
            260                 265                 270

Glu Leu Lys Arg Gly Pro Gly Asp Lys Thr His Thr Cys Pro Pro Cys
        275                 280                 285

Pro Ala Pro Glu Leu Leu Gly Gly Pro Ser Val Phe Leu Phe Pro Pro
        290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
            355                 360                 365

His Gln Asp Trp Leu Asn Gly Lys Glu Tyr Lys Cys Lys Val Ser Asn
        370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Asp Glu
                405                 410                 415

Leu Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445
```

```
Asn Tyr Lys Thr Thr Pro Pro Val Leu Asp Ser Asp Gly Ser Phe Phe
            450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys Gly Gly Gly Ser Gly
            500                 505                 510

Ala Pro Phe Arg Asp Cys Ala Glu Val Phe Lys Ser Gly His Thr Thr
            515                 520                 525

Asn Gly Ile Tyr Thr Leu Thr Phe Pro Asn Ser Thr Glu Glu Ile Lys
            530                 535                 540

Ala Tyr Cys Asp Met Glu Ala Gly Gly Gly Gly Trp Thr Ile Ile Gln
545                 550                 555                 560

Arg Arg Glu Asp Gly Ser Val Asp Phe Gln Arg Thr Trp Lys Glu Tyr
                565                 570                 575

Lys Val Gly Phe Gly Asn Pro Ser Gly Glu Tyr Trp Leu Gly Asn Glu
            580                 585                 590

Phe Val Ser Gln Leu Thr Asn Gln Gln Arg Tyr Val Leu Lys Ile His
            595                 600                 605

Leu Lys Asp Trp Glu Gly Asn Glu Ala Tyr Ser Leu Tyr Glu His Phe
            610                 615                 620

Tyr Leu Ser Ser Glu Glu Leu Asn Tyr Arg Ile His Leu Lys Gly Leu
625                 630                 635                 640

Thr Gly Thr Ala Gly Lys Ile Ser Ser Ile Ser Gln Pro Gly Asn Asp
                645                 650                 655

Phe Ser Thr Lys Asp Gly Asp Asn Asp Lys Cys Ile Cys Lys Cys Ser
                660                 665                 670

Gln Met Leu Thr Gly Gly Trp Trp Phe Asp Ala Cys Gly Pro Ser Asn
            675                 680                 685

Leu Asn Gly Met Tyr Tyr Pro Gln Arg Gln Asn Thr Asn Lys Phe Asn
            690                 695                 700

Gly Ile Lys Trp Tyr Tyr Trp Lys Gly Ser Gly Tyr Ser Leu Lys Ala
705                 710                 715                 720

Thr Thr Met Met Ile Arg Pro Ala Asp Phe
                725                 730

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Gly Gly Gly Gly Ser Gly Ala Pro
1               5

<210> SEQ ID NO 33
<211> LENGTH: 27
<212> TYPE: DNA
<213> ORGANISM: Artificial Sequence
<220> FEATURE:
<223> OTHER INFORMATION: Primers

<400> SEQUENCE: 33
atagacagat gggggtgtcg ttttggc                                      27
```

<210> SEQ ID NO 34
<211> LENGTH: 21
<212> TYPE: DNA
<213> ORGANISM: Artificial Sequence
<220> FEATURE:
<223> OTHER INFORMATION: Primers

<400> SEQUENCE: 34
ggatacagtt ggtgcagcat c                                           21

<210> SEQ ID NO 35
<211> LENGTH: 39
<212> TYPE: DNA
<213> ORGANISM: Artificial Sequence
<220> FEATURE:
<223> OTHER INFORMATION: Primers

<400> SEQUENCE: 35
ggggatatcc accatggrat gsagctgkgt matsctctt                        39

<210> SEQ ID NO 36
<211> LENGTH: 39
<212> TYPE: DNA
<213> ORGANISM: Artificial Sequence
<220> FEATURE:
<223> OTHER INFORMATION: Primers

<400> SEQUENCE: 36
ggggatatcc accatgract tcgggytgag ctkggtttt                        39

<210> SEQ ID NO 37
<211> LENGTH: 38
<212> TYPE: DNA
<213> ORGANISM: Artificial Sequence
<220> FEATURE:
<223> OTHER INFORMATION: Primers

<400> SEQUENCE: 37
ggggatatcc accatggctg tcttggggct gctcttct                         38

<210> SEQ ID NO 38
<211> LENGTH: 39
<212> TYPE: DNA
<213> ORGANISM: Artificial Sequence
<220> FEATURE:
<223> OTHER INFORMATION: Primers

<400> SEQUENCE: 38
ggggatatcc accatggatt ttcaggtgca gattttcag                        39

<210> SEQ ID NO 39
<211> LENGTH: 40
<212> TYPE: DNA
<213> ORGANISM: Artificial Sequence
<220> FEATURE:
<223> OTHER INFORMATION: Primers

<400> SEQUENCE: 39
ggggatatcc accatgragt cacakacyca ggtcttyrta                       40

<210> SEQ ID NO 40
<211> LENGTH: 40
<212> TYPE: DNA
<213> ORGANISM: Artificial Sequence
<220> FEATURE:

<223> OTHER INFORMATION: Primers

<400> SEQUENCE: 40 gggatatcc accatgaggk ccccwgctca gytyctkggr         40

<210> SEQ ID NO 41
<211> LENGTH: 37
<212> TYPE: DNA
<213> ORGANISM: Artificial Sequence
<220> FEATURE:
<223> OTHER INFORMATION: Primers

<400> SEQUENCE: 41
ggggatatcc accatgaagt tgcttgttag gctgttg          37

<210> SEQ ID NO 42
<211> LENGTH: 43
<212> TYPE: DNA
<213> ORGANISM: Artificial Sequence
<220> FEATURE:
<223> OTHER INFORMATION: Primers

<400> SEQUENCE: 42
gatcggcgcg cctgatgtgc agctggtgga gtctggggga ggc    43

<210> SEQ ID NO 43
<211> LENGTH: 63
<212> TYPE: DNA
<213> ORGANISM: Artificial Sequence
<220> FEATURE:
<223> OTHER INFORMATION: Primers

<400> SEQUENCE: 43
gccggagccc ccgccccgg aacctccacc tcctgaggag acggtgactg aggttccttg   60
acc                                              63

<210> SEQ ID NO 44
<211> LENGTH: 63
<212> TYPE: DNA
<213> ORGANISM: Artificial Sequence
<220> FEATURE:
<223> OTHER INFORMATION: Primers

<400> SEQUENCE: 44
tccgggggcg ggggctccgg cggaggtgga tcagacatcc agatgactca gtctccagcc   60
tcc                                              63

<210> SEQ ID NO 45
<211> LENGTH: 54
<212> TYPE: DNA
<213> ORGANISM: Artificial Sequence
<220> FEATURE:
<223> OTHER INFORMATION: Primers

<400> SEQUENCE: 45
cgatgcggcc gctcagcccg ggccccgttt gatttccagc ttggtgcctc cacc        54

<210> SEQ ID NO 46
<211> LENGTH: 43
<212> TYPE: DNA
<213> ORGANISM: Artificial Sequence
<220> FEATURE:
<223> OTHER INFORMATION: Primers

<400> SEQUENCE: 46

```
gatcggcgcg cctgaagtga agctggtgga gtctggggga ggc          43
```

<210> SEQ ID NO 47
<211> LENGTH: 63
<212> TYPE: DNA
<213> ORGANISM: Artificial Sequence
<220> FEATURE:
<223> OTHER INFORMATION: Primers

<400> SEQUENCE: 47

```
gccggagccc ccgccccggg aacctccacc tcctgaggag acggtgactg aggttccttg   60
acc                                                                 63
```

<210> SEQ ID NO 48
<211> LENGTH: 63
<212> TYPE: DNA
<213> ORGANISM: Artificial Sequence
<220> FEATURE:
<223> OTHER INFORMATION: Primers

<400> SEQUENCE: 48

```
tccgggggcg ggggctccgg cggaggtgga tcagatatcc agatgacaca gactacatcc   60
tcc                                                                 63
```

<210> SEQ ID NO 49
<211> LENGTH: 54
<212> TYPE: DNA
<213> ORGANISM: Artificial Sequence
<220> FEATURE:
<223> OTHER INFORMATION: Primers

<400> SEQUENCE: 49

```
cgatgcggcc gctcagcccg ggccccgttt tatttccagc ttggtccccc ctcc         54
```

<210> SEQ ID NO 50
<211> LENGTH: 734
<212> TYPE: PRT
<213> ORGANISM: Artificial Sequence
<220> FEATURE:
<223> OTHER INFORMATION: Synthetic

<400> SEQUENCE: 50

Gly Ala Pro Asp Val Gln Leu Val Glu Ser Gly Gly Gly Leu Val Gln
1               5                   10                  15

Pro Gly Gly Ser Arg Lys Leu Ser Cys Ala Ala Ser Gly Phe Thr Phe
            20                  25                  30

Ser Ser Phe Gly Met His Trp Val Arg Gln Ala Pro Glu Lys Gly Leu
        35                  40                  45

Glu Trp Val Ala Tyr Ile Ser Ser Gly Ser Ser Asn Ile Tyr Tyr Ala
    50                  55                  60

Asp Thr Val Lys Gly Arg Phe Thr Ile Ser Arg Asp Asn Pro Lys Asn
65                  70                  75                  80

Thr Leu Phe Leu Gln Met Thr Ser Leu Arg Ser Glu Asp Thr Ala Met
                85                  90                  95

Tyr Tyr Cys Ala Arg Gly Tyr Asp Tyr Asp Arg Gly Tyr Tyr Ala Ile
            100                 105                 110

Asp Tyr Trp Gly Gln Gly Thr Ser Val Thr Val Ser Ser Gly Gly Gly
        115                 120                 125

Gly Ser Gly Gly Gly Gly Ser Gly Gly Gly Gly Ser Asp Ile Gln Met
    130                 135                 140

```
Thr Gln Ser Pro Ala Ser Leu Ser Ala Ser Val Gly Glu Thr Val Thr
145                 150                 155                 160

Ile Thr Cys Arg Ala Ser Glu Asn Ile Tyr Ser Asn Leu Ala Trp Tyr
            165                 170                 175

Gln Gln Lys Gln Gly Lys Ser Pro Gln Leu Leu Val Tyr Gly Ala Thr
        180                 185                 190

Asn Leu Ala Asp Gly Val Pro Ser Arg Phe Ser Gly Ser Gly Ser Gly
            195                 200                 205

Thr Gln Tyr Ser Leu Lys Ile Asn Ser Leu Gln Ser Glu Asp Phe Gly
210                 215                 220

Ser Tyr Tyr Cys Gln His Phe Trp Gly Thr Pro Trp Thr Leu Gly Gly
225                 230                 235                 240

Gly Thr Lys Leu Glu Ile Lys Arg Gly Pro Gly Asp Lys Thr His Thr
            245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
            325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
            450                 455                 460

Asn His Tyr Thr Gln Lys Ser Leu Ser Leu Ser Pro Gly Lys Gly Gly
465                 470                 475                 480

Gly Gly Ser Gly Ala Pro Asp Val Gln Leu Val Glu Ser Gly Gly Gly
                485                 490                 495

Leu Val Gln Pro Gly Gly Ser Arg Lys Leu Ser Cys Ala Ala Ser Gly
            500                 505                 510

Phe Thr Phe Ser Ser Phe Gly Met His Trp Val Arg Gln Ala Pro Glu
            515                 520                 525

Lys Gly Leu Glu Trp Val Ala Tyr Ile Ser Ser Gly Ser Ser Asn Ile
            530                 535                 540

Tyr Tyr Ala Asp Thr Val Lys Gly Arg Phe Thr Ile Ser Arg Asp Asn
545                 550                 555                 560
```

```
Pro Lys Asn Thr Leu Phe Leu Gln Met Thr Ser Leu Arg Ser Glu Asp
                565                 570                 575

Thr Ala Met Tyr Tyr Cys Ala Arg Gly Tyr Asp Tyr Asp Arg Gly Tyr
            580                 585                 590

Tyr Ala Ile Asp Tyr Trp Gly Gln Gly Thr Ser Val Thr Val Ser Ser
            595                 600                 605

Gly Gly Gly Gly Ser Gly Gly Gly Ser Gly Gly Gly Ser Asp
            610                 615                 620

Ile Gln Met Thr Gln Ser Pro Ala Ser Leu Ala Ser Val Gly Glu
625                 630                 635                 640

Thr Val Thr Ile Thr Cys Arg Ala Ser Glu Asn Ile Tyr Ser Asn Leu
                645                 650                 655

Ala Trp Tyr Gln Gln Lys Gln Gly Lys Ser Pro Gln Leu Leu Val Tyr
            660                 665                 670

Gly Ala Thr Asn Leu Ala Asp Gly Val Pro Ser Arg Phe Ser Gly Ser
            675                 680                 685

Gly Ser Gly Thr Gln Tyr Ser Leu Lys Ile Asn Ser Leu Gln Ser Glu
            690                 695                 700

Asp Phe Gly Ser Tyr Tyr Cys Gln His Phe Trp Gly Thr Pro Trp Thr
705                 710                 715                 720

Leu Gly Gly Gly Thr Lys Leu Glu Ile Lys Arg Gly Pro Gly
                725                 730

<210> SEQ ID NO 51
<211> LENGTH: 731
<212> TYPE: PRT
<213> ORGANISM: Artificial Sequence
<220> FEATURE:
<223> OTHER INFORMATION: Synthetic

<400> SEQUENCE: 51

Gly Ala Pro Glu Val Lys Leu Val Glu Ser Gly Gly Gly Leu Val Lys
1               5                   10                  15

Pro Gly Gly Ser Leu Lys Leu Ser Cys Ala Ala Ser Gly Phe Thr Phe
            20                  25                  30

Ser Ser Tyr Gly Met Ser Trp Val Arg Gln Thr Pro Glu Lys Arg Leu
        35                  40                  45

Glu Trp Val Ala Thr Ile Ser Gly Gly Ser Tyr Thr Tyr Tyr Pro
50                  55                  60

Asp Ser Val Lys Gly Arg Phe Thr Ile Ser Arg Asp Asn Ala Lys Asn
65                  70                  75                  80

Asn Leu Tyr Leu Gln Met Ser Ser Leu Arg Ser Glu Asp Thr Ala Leu
                85                  90                  95

Tyr Tyr Cys Ala Arg Arg Arg Tyr Asp Pro Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Asp Ile Gln Met Thr Gln Thr
            130                 135                 140

Thr Ser Ser Leu Ser Ala Ser Leu Gly Asp Arg Val Thr Ile Ser Cys
145                 150                 155                 160

Arg Ala Ser Gln Asp Ile Ser Asn Tyr Leu Asn Trp Tyr Gln Gln Lys
                165                 170                 175

Pro Asp Gly Thr Val Lys Leu Leu Ile Tyr Tyr Ile Ser Arg Leu His
            180                 185                 190
```

```
Ser Gly Val Pro Ser Arg Phe Ser Gly Ser Gly Ser Gly Thr Asp Tyr
            195                 200                 205
Ser Leu Thr Ile Ser Asn Leu Glu Gln Glu Asp Ile Ala Thr Tyr Phe
210                 215                 220
Cys Gln Gln Gly Asn Thr Leu Pro Tyr Thr Phe Gly Gly Gly Thr Lys
225                 230                 235                 240
Leu Glu Ile Lys Arg Gly Pro Gly Asp Lys Thr His Thr Cys Pro Pro
            245                 250                 255
Cys Pro Ala Pro Glu Leu Leu Gly Gly Pro Ser Val Phe Leu Phe Pro
            260                 265                 270
Pro Lys Pro Lys Asp Thr Leu Met Ile Ser Arg Thr Pro Glu Val Thr
            275                 280                 285
Cys Val Val Val Asp Val Ser His Glu Asp Pro Glu Val Lys Phe Asn
290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Glu Tyr Lys Cys Lys Val Ser
            340                 345                 350
Asn Lys Ala Leu Pro Ala Pro Ile Glu Lys Thr Ile Ser Lys Ala Lys
            355                 360                 365
Gly Gln Pro Arg Glu Pro Gln Val Tyr Thr Leu Pro Pro Ser Arg Asp
            370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
            405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
            435                 440                 445
Asn Val Phe Ser Cys Ser Val Met His Glu Ala Leu His Asn His Tyr
450                 455                 460
Thr Gln Lys Ser Leu Ser Leu Ser Pro Gly Lys Gly Gly Gly Gly Ser
465                 470                 475                 480
Gly Ala Pro Asp Val Gln Leu Val Glu Ser Gly Gly Gly Leu Val Gln
            485                 490                 495
Pro Gly Gly Ser Arg Lys Leu Ser Cys Ala Ala Ser Gly Phe Thr Phe
            500                 505                 510
Ser Ser Phe Gly Met His Trp Val Arg Gln Ala Pro Glu Lys Gly Leu
            515                 520                 525
Glu Trp Val Ala Tyr Ile Ser Ser Gly Ser Ser Asn Ile Tyr Tyr Ala
530                 535                 540
Asp Thr Val Lys Gly Arg Phe Thr Ile Ser Arg Asp Asn Pro Lys Asn
545                 550                 555                 560
Thr Leu Phe Leu Gln Met Thr Ser Leu Arg Ser Glu Asp Thr Ala Met
            565                 570                 575
Tyr Tyr Cys Ala Arg Gly Tyr Asp Tyr Asp Arg Gly Tyr Tyr Ala Ile
            580                 585                 590
Asp Tyr Trp Gly Gln Gly Thr Ser Val Thr Val Ser Ser Gly Gly Gly
            595                 600                 605
Gly Ser Gly Gly Gly Gly Ser Gly Gly Gly Gly Ser Asp Ile Gln Met
```

```
                    610                 615                 620
Thr Gln Ser Pro Ala Ser Leu Ser Ala Ser Val Gly Glu Thr Val Thr
625                 630                 635                 640

Ile Thr Cys Arg Ala Ser Glu Asn Ile Tyr Ser Asn Leu Ala Trp Tyr
                    645                 650                 655

Gln Gln Lys Gln Gly Lys Ser Pro Gln Leu Leu Val Tyr Gly Ala Thr
                660                 665                 670

Asn Leu Ala Asp Gly Val Pro Ser Arg Phe Ser Gly Ser Gly Ser Gly
                675                 680                 685

Thr Gln Tyr Ser Leu Lys Ile Asn Ser Leu Gln Ser Glu Asp Phe Gly
                690                 695                 700

Ser Tyr Tyr Cys Gln His Phe Trp Gly Thr Pro Trp Thr Leu Gly Gly
705                 710                 715                 720

Gly Thr Lys Leu Glu Ile Lys Arg Gly Pro Gly
                725                 730
```

<210> SEQ ID NO 52
<211> LENGTH: 702
<212> TYPE: PRT
<213> ORGANISM: Artificial Sequence
<220> FEATURE:
<223> OTHER INFORMATION: Synthetic

<400> SEQUENCE: 52

```
Gly Ala Pro Asp Val Gln Leu Val Glu Ser Gly Gly Gly Leu Val Gln
1               5                   10                  15

Pro Gly Gly Ser Arg Lys Leu Ser Cys Ala Ala Ser Gly Phe Thr Phe
                20                  25                  30

Ser Ser Phe Gly Met His Trp Val Arg Gln Ala Pro Glu Lys Gly Leu
                35                  40                  45

Glu Trp Val Ala Tyr Ile Ser Ser Gly Ser Ser Asn Ile Tyr Tyr Ala
                50                  55                  60

Asp Thr Val Lys Gly Arg Phe Thr Ile Ser Arg Asp Asn Pro Lys Asn
65                  70                  75                  80

Thr Leu Phe Leu Gln Met Thr Ser Leu Arg Ser Glu Asp Thr Ala Met
                85                  90                  95

Tyr Tyr Cys Ala Arg Gly Tyr Asp Tyr Asp Arg Gly Tyr Tyr Ala Ile
                100                 105                 110

Asp Tyr Trp Gly Gln Gly Thr Ser Val Thr Val Ser Ser Gly Gly Gly
                115                 120                 125

Gly Ser Gly Gly Gly Gly Ser Gly Gly Gly Gly Ser Asp Ile Gln Met
130                 135                 140

Thr Gln Ser Pro Ala Ser Leu Ser Ala Ser Val Gly Glu Thr Val Thr
145                 150                 155                 160

Ile Thr Cys Arg Ala Ser Glu Asn Ile Tyr Ser Asn Leu Ala Trp Tyr
                165                 170                 175

Gln Gln Lys Gln Gly Lys Ser Pro Gln Leu Leu Val Tyr Gly Ala Thr
                180                 185                 190

Asn Leu Ala Asp Gly Val Pro Ser Arg Phe Ser Gly Ser Gly Ser Gly
                195                 200                 205

Thr Gln Tyr Ser Leu Lys Ile Asn Ser Leu Gln Ser Glu Asp Phe Gly
                210                 215                 220

Ser Tyr Tyr Cys Gln His Phe Trp Gly Thr Pro Trp Thr Leu Gly Gly
225                 230                 235                 240

Gly Thr Lys Leu Glu Ile Lys Arg Gly Pro Gly Asp Lys Thr His Thr
```

-continued

```
                245                 250                 255
Cys Pro Pro Cys Pro Ala Pro Glu Leu Leu Gly Gly Pro Ser Val Phe
            260                 265                 270
Leu Phe Pro Pro Lys Pro Lys Asp Thr Leu Met Ile Ser Arg Thr Pro
            275                 280                 285
Glu Val Thr Cys Val Val Val Asp Val Ser His Glu Asp Pro Glu Val
            290                 295                 300
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
            325                 330                 335
Leu Thr Val Leu His Gln Asp Trp Leu Asn Gly Lys Glu Tyr Lys Cys
            340                 345                 350
Lys Val Ser Asn Lys Ala Leu Pro Ala Pro Ile Glu Lys Thr Ile Ser
            355                 360                 365
Lys Ala Lys Gly Gln Pro Arg Glu Pro Gln Val Tyr Thr Leu Pro Pro
            370                 375                 380
Ser Arg Asp Glu Leu Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
            405                 410                 415
Gln Pro Glu Asn Asn Tyr Lys Thr Thr Pro Pro Val Leu Asp Ser Asp
            420                 425                 430
Gly Ser Phe Phe Leu Tyr Ser Lys Leu Thr Val Asp Lys Ser Arg Trp
            435                 440                 445
Gln Gln Gly Asn Val Phe Ser Cys Ser Val Met His Glu Ala Leu His
            450                 455                 460
Asn His Tyr Thr Gln Lys Ser Leu Ser Leu Ser Pro Gly Lys Gly Gly
465                 470                 475                 480
Gly Gly Ser Gly Ala Pro Phe Arg Asp Cys Ala Asp Val Tyr Gln Ala
            485                 490                 495
Gly Phe Asn Lys Ser Gly Ile Tyr Thr Ile Tyr Ile Asn Asn Met Pro
            500                 505                 510
Glu Pro Lys Lys Val Phe Cys Asn Met Asp Val Asn Gly Gly Gly Trp
            515                 520                 525
Thr Val Ile Gln His Arg Glu Asp Gly Ser Leu Asp Phe Gln Arg Gly
            530                 535                 540
Trp Lys Glu Tyr Lys Met Gly Phe Gly Asn Pro Ser Gly Glu Tyr Trp
545                 550                 555                 560
Leu Gly Asn Glu Phe Ile Phe Ala Ile Thr Ser Gln Arg Gln Tyr Met
            565                 570                 575
Leu Arg Ile Glu Leu Met Asp Trp Glu Gly Asn Arg Ala Tyr Ser Gln
            580                 585                 590
Tyr Asp Arg Phe His Ile Gly Asn Glu Lys Gln Asn Tyr Arg Leu Tyr
            595                 600                 605
Leu Lys Gly His Thr Gly Thr Ala Gly Lys Gln Ser Ser Leu Ile Leu
            610                 615                 620
His Gly Ala Asp Phe Ser Thr Lys Asp Ala Asp Asn Asp Asn Cys Met
625                 630                 635                 640
Cys Lys Cys Ala Leu Met Leu Thr Gly Gly Trp Trp Phe Asp Ala Cys
            645                 650                 655
Gly Pro Ser Asn Leu Asn Gly Met Phe Tyr Thr Ala Gly Gln Asn His
            660                 665                 670
```

-continued

Gly Lys Leu Asn Gly Ile Lys Trp His Tyr Phe Lys Gly Pro Ser Tyr
            675                 680                 685

Ser Leu Arg Ser Thr Thr Met Met Ile Arg Pro Leu Asp Phe
    690                 695                 700

<210> SEQ ID NO 53
<211> LENGTH: 702
<212> TYPE: PRT
<213> ORGANISM: Artificial Sequence
<220> FEATURE:
<223> OTHER INFORMATION: Synthetic

<400> SEQUENCE: 53

Gly Ala Pro Asp Val Gln Leu Val Glu Ser Gly Gly Leu Val Gln
1               5                   10                  15

Pro Gly Gly Ser Arg Lys Leu Ser Cys Ala Ala Ser Gly Phe Thr Phe
                20                  25                  30

Ser Ser Phe Gly Met His Trp Val Arg Gln Ala Pro Glu Lys Gly Leu
            35                  40                  45

Glu Trp Val Ala Tyr Ile Ser Ser Gly Ser Ser Asn Ile Tyr Tyr Ala
    50                  55                  60

Asp Thr Val Lys Gly Arg Phe Thr Ile Ser Arg Asp Asn Pro Lys Asn
65                  70                  75                  80

Thr Leu Phe Leu Gln Met Thr Ser Leu Arg Ser Glu Asp Thr Ala Met
                85                  90                  95

Tyr Tyr Cys Ala Arg Gly Tyr Asp Tyr Asp Arg Gly Tyr Tyr Ala Ile
                100                 105                 110

Asp Tyr Trp Gly Gln Gly Thr Ser Val Thr Val Ser Ser Gly Gly Gly
            115                 120                 125

Gly Ser Gly Gly Gly Gly Ser Gly Gly Gly Gly Ser Asp Ile Gln Met
            130                 135                 140

Thr Gln Ser Pro Ala Ser Leu Ser Ala Ser Val Gly Glu Thr Val Thr
145                 150                 155                 160

Ile Thr Cys Arg Ala Ser Glu Asn Ile Tyr Ser Asn Leu Ala Trp Tyr
                165                 170                 175

Gln Gln Lys Gln Gly Lys Ser Pro Gln Leu Leu Val Tyr Gly Ala Thr
            180                 185                 190

Asn Leu Ala Asp Gly Val Pro Ser Arg Phe Ser Gly Ser Gly Ser Gly
        195                 200                 205

Thr Gln Tyr Ser Leu Lys Ile Asn Ser Leu Gln Ser Glu Asp Phe Gly
    210                 215                 220

Ser Tyr Tyr Cys Gln His Phe Trp Gly Thr Pro Trp Thr Leu Gly Gly
225                 230                 235                 240

Gly Thr Lys Leu Glu Ile Lys Arg Gly Pro Gly Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

-continued

```
Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Tyr Thr Leu Pro Pro
            370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
            450                 455                 460

Asn His Tyr Thr Gln Lys Ser Leu Ser Leu Ser Pro Gly Lys Gly Gly
465                 470                 475                 480

Gly Gly Ser Gly Ala Pro Phe Arg Asp Cys Ala Glu Val Phe Lys Ser
                485                 490                 495

Gly His Thr Thr Asn Gly Ile Tyr Thr Leu Thr Phe Pro Asn Ser Thr
            500                 505                 510

Glu Glu Ile Lys Ala Tyr Cys Asp Met Glu Ala Gly Gly Gly Gly Trp
            515                 520                 525

Thr Ile Ile Gln Arg Arg Glu Asp Gly Ser Val Asp Phe Gln Arg Thr
            530                 535                 540

Trp Lys Glu Tyr Lys Val Gly Phe Gly Asn Pro Ser Gly Glu Tyr Trp
545                 550                 555                 560

Leu Gly Asn Glu Phe Val Ser Gln Leu Thr Asn Gln Gln Arg Tyr Val
                565                 570                 575

Leu Lys Ile His Leu Lys Asp Trp Glu Gly Asn Glu Ala Tyr Ser Leu
            580                 585                 590

Tyr Glu His Phe Tyr Leu Ser Ser Glu Glu Leu Asn Tyr Arg Ile His
            595                 600                 605

Leu Lys Gly Leu Thr Gly Thr Ala Gly Lys Ile Ser Ser Ile Ser Gln
            610                 615                 620

Pro Gly Asn Asp Phe Ser Thr Lys Asp Gly Asp Asn Asp Lys Cys Ile
625                 630                 635                 640

Cys Lys Cys Ser Gln Met Leu Thr Gly Gly Trp Trp Phe Asp Ala Cys
                645                 650                 655

Gly Pro Ser Asn Leu Asn Gly Met Tyr Tyr Pro Gln Arg Gln Asn Thr
            660                 665                 670

Asn Lys Phe Asn Gly Ile Lys Trp Tyr Tyr Trp Lys Gly Ser Gly Tyr
            675                 680                 685

Ser Leu Lys Ala Thr Thr Met Met Ile Arg Pro Ala Asp Phe
            690                 695                 700
```

FUSION POLYPEPTIDES CAPABLE OF ACTIVATING RECEPTORS

CROSS-REFERENCE TO RELATED APPLICATIONS

This application is a continuation of U.S. Ser. No. 14/511,786, filed 10 Oct. 2014, which is a continuation of U.S. Ser. No. 13/857,551, filed 5 Apr. 2013, now U.S. Pat. No. 8,927,233, which is a continuation of U.S. Ser. No. 13/628,082, filed 27 Sep. 2012, now U.S. Pat. No. 8,470,324, which is a continuation of U.S. Ser. No. 12/466,606, filed 15 May 2009, now U.S. Pat. No. 8,298,532, which is a continuation-in-part of U.S. Ser. No. 11/035,599, filed 14 Jan. 2005, now U.S. Pat. No. 7,534,604, which claims the benefit under 35 USC § 119(e) of U.S. Provisional 60/536,968 filed 16 Jan. 2004, which applications are hereby incorporated by reference.

FIELD OF THE INVENTION

This invention relates to multimeric fusion proteins capable of activating a target receptor, methods of producing such fusion polypeptides, and methods for treating, diagnosing, or monitoring diseases or conditions in which activation of the target receptor is desired.

BACKGROUND

The clustering of soluble Eph ligand domains to create multimers capable of activating their cognate receptors is described in U.S. Pat. No. 5,747,033. U.S. Pat. No. 6,319,499 recites a method of activating an erythropoietin receptor with an antibody.

BRIEF SUMMARY

The present invention provides multimeric fusion polypeptides capable of activating a target receptor requiring multimerization to be activated. The polypeptides of the invention are useful for treating conditions in which activation of a target receptor is desirable, as well as having a variety of in vitro and in vivo diagnostic and prognostic uses. The polypeptides of the invention may be monospecific or bispecific tetramers exhibiting improved capacity to activate a target receptor relative to, for example, a target-specific antibody or the natural ligand.

Accordingly, in one aspect the invention provides an isolated nucleic acid molecule which encodes a fusion polypeptide $(A)_x$-M-$(A')_y$, wherein A is a polypeptide specific for a target receptor, M is a multimerizing component, A' is a polypeptide specific for the same target receptor as A, and X and Y are independently a number between 1-10.

In a first embodiment, A and A' are antibodies or antibody fragments specific to the target receptor, and are the same antibody or antibody fragment specific to a target receptor. In another embodiment, A and A' are different antibodies or antibody fragments specific to the same target receptor. Preferably, A and A' are single chain Fv (scFv) fragments. When the fusion polypeptide is intended as a human therapeutic, the invention encompasses humanized antibody or antibody fragments.

In a second embodiment, A and A' are ligands or ligand fragments specific for the same target receptor. In a more specific embodiment, A and A' are the same or are different ligands or ligand fragments specific to the same target receptor.

In a third embodiment, A is an antibody or antibody fragment specific to the target receptor, and A' is a ligand or ligand fragment specific to the same target receptor. In preferred embodiments, A is an antibody or antibody fragment to a Tie receptor (Tie-1 or Tie-2), and A' is the fibrinogen domain of a Tie receptor.

In specific embodiments, M is a multimerizing component which multimerizes with a multimerizing component on another fusion polypeptide to form a multimer of the fusion polypeptides. In a preferred embodiment, M is the Fc domain of IgG or the heavy chain of IgG. The Fc domain of IgG may be selected from the isotypes $IgG_1$, $IgG_2$, $IgG_3$, and $IgG_4$, as well as any allotype within each isotype group.

In another aspect the invention provides a fusion polypeptide comprising $(A)_x$-M-$(A')_y$, wherein A is a polypeptide specific for a target receptor, M is a multimerizing component, A' is a polypeptide specific for the same target receptor as A, and X and Y are independently a number between 1-10.

In a first embodiment, A and A' are antibodies or antibody fragments specific to the target receptor, and are the same antibody or antibody fragment specific to a target receptor. In another embodiment, A and A' are different antibodies or antibody fragments specific to the same target receptor. Preferably, A and A' are single chain Fv fragments (scFvs).

In a second embodiment, A and A' are ligands or ligand fragments specific for the same target receptor. In a more specific embodiment, A and A' are different ligands or ligand fragments specific to the same target receptor. In another specific embodiment, A and A' are the same ligand or ligand fragment.

In a third embodiment, A is an antibody or antibody fragment specific to the target receptor, and A' is a ligand or ligand fragment specific to the same target receptor.

In another aspect, the invention provides an activating dimeric fusion polypeptide comprising two fusion polypeptides of the invention, e.g., a dimer formed from two polypeptides of $(A)_x$-M-$(A')_y$ as defined above. The activating dimers of the invention are capable of binding to and clustering four or more receptors, leading to receptor activation, as compared with the ability of an antibody to cluster no more than two receptors.

In one embodiment, the components of the fusion polypeptides of the invention are connected directly to each other. In other embodiments, a spacer sequence may be included between one or more components, which may comprise one or more molecules, such as amino acids. For example, a spacer sequence may include one or more amino acids naturally connected to a domain-containing component. A spacer sequence may also include a sequence used to enhance expression of the fusion polypeptide, provide restriction sites, allow component domains to form optimal tertiary and quaternary structures and/or to enhance the interaction of a component with its target receptor. In one embodiment, the fusion polypeptide of the invention comprises one or more peptide sequences between one or more components which is(are) between 1-25 amino acids. Further embodiments may include a signal sequence at the beginning or amino-terminus of an fusion polypeptide of the invention. Such a signal sequence may be native to the cell, recombinant, or synthetic.

The components of the fusion polypeptide of the invention may be arranged in a variety of configurations. For example, described from the beginning or amino-terminus of the fusion polypeptide, $(A)_x$-M-$(A')_y$, $(A)_x$-$(A')_y$-M, M-$(A)_x$-$(A')_y$, $(A')_y$-M-$(A)_x$, $(A')_y$-$(A)_x$-M, M-$(A')_y$-$(A)_x$, $(A)_x$-M-$(A')_y$, $(A)_x$-$(A')_y$-M, M-$(A)_x$-$(A')_y$, etc., wherein X=1-10 and Y=1-10. In an even more specific embodiment, X=1, and Y=1 or X=2 and Y=2.

In one aspect, a Tie receptor (i.e., Tie)-binding protein comprising fusion polypeptide A-M-A' is provided, wherein: (a) A comprises a Tie-binding fragment of an antibody that binds a Tie-2 receptor (i.e., Tie-2) on the surface of a cell; (b) A' is selected from (i) an antibody fragment that binds Tie-2, and (ii) a fibrinogen domain of Ang-1 (FD1) or Ang-2 (FD2), or Tie-binding fragment thereof; and (c) M is a multimerizing component; wherein binding of A to Tie-2 does not block binding of A' to Tie-2.

In one embodiment, the Tie-binding protein when exposed to a cell bearing a Tie-1, activates Tie-1 and Tie-1 is phosphorylated. In one embodiment, the Tie-binding protein when exposed to a cell bearing a Tie-2 activates the Tie-2 and Tie-2 is phosphorylated. In one embodiment, the Tie-binding protein when exposed to a cell bearing a Tie-1 and a Tie-2, both Tie-1 and Tie-2 are phosphorylated. In one embodiment, the phosphorylation is more than two-fold higher than a Tie-binding protein wherein A and A' block one another, as measured by immunoprecipitation of total Tie-1 and/or total Tie-2 and detecting phosphotyrosine. In another embodiment, the phosphorylation is more than four-fold. In another embodiment, more than ten-fold.

In one embodiment, the Tie-binding protein binds Tie-2 with higher affinity than FD1. In one embodiment, exposing a cell bearing a Tie-2 to the Tie-binding protein results in clustering of more than four Tie receptors of the cell. In one embodiment, exposing a cell bearing a Tie-2 to the Tie-binding protein results in phosphorylation and activation of a Tie-2 and a Tie-1 of the cell.

In one embodiment, the cell is a mammalian cell selected from a mouse, rat, hamster, monkey, ape, and human cell. In one embodiment, the Tie-2 is selected from mouse, rat, hamster, monkey, ape, and human Tie-2. In a specific embodiment, the Tie-2 is a human Tie-2.

In one embodiment, the Tie-binding protein comprises an A and/or an A' that is an scFv.

In one embodiment, A (or A') comprises FD1 or FD2 or a Tie-binding fragment thereof.

In one embodiment, the FD1 comprises amino acids 515-728 of SEQ ID NO:30. In one embodiment, the FD2 comprises amino acids 515-727 of SEQ ID NO:31.

In one embodiment, M is selected from the group consisting of an Fc domain of IgG, and a polypeptide comprising a heavy chain $CH_2$ and $CH_3$ constant region. In one embodiment, M is an Fc domain of an IgG that lacks a $CH_1$ domain. In one embodiment, the Fc domain comprises amino acids 281-507 of SEQ ID NO:28.

In one embodiment, the Tie-binding protein comprises, from N-terminal to C-terminal (a) a first Tie-binding region comprising a first scFv that comprises a CDR comprising a sequence selected from: amino acids 58-65 (HCDR1), 83-90 (HCDR2), 129-139 (HCDR3), 192-201 (LCDR1), 219-221 (LCDR2), 258-265 (LCDR3) of SEQ ID NO:28, wherein the first scFv binds a first epitope of Tie-2; (b) a multimerizing component; and (c) a second Tie-binding region comprising either (i) a second scFv that comprises a CDR that binds a second epitope of Tie-2, or (ii) an FD1 or FD2, or Tie-binding fragment thereof. In one embodiment, the second scFv comprises three HCDRs and three LCDRs.

In one embodiment, the Tie-binding protein comprises, from N-terminal to C-terminal (a) a first Tie-binding region comprising a first scFv that comprises a CDR comprising a sequence selected from: amino acids 58-66 (HCDR1), 84-90 (HCDR2), 129-143 (HCDR3), 196-201 (LCDR1), 219-221 (LCDR2), 258-265 (LCDR3) of SEQ ID NO:29, wherein the first scFv binds a first epitope of Tie-2; (b) a multimerizing component; and (c) a second Tie-binding region comprising either (i) a second scFv that comprises a CDR that binds a second epitope of Tie-2, or (ii) an FD1 or FD2, or Tie-binding fragment thereof. In one embodiment, the second scFv comprises three HCDRs and three LCDRs.

In one embodiment, the Tie-binding protein comprises a first polypeptide comprising first scFv comprising three HCDRs (amino acids 58-65 (HCDR1), 83-90 (HCDR2), 129-139(HCDR3) of SEQ ID NO:28) and three LCDRs (amino acids 192-201 (LCDR1), 219-221 (LCDR2), 258-265 (LCDR3) of SEQ ID NO:28), wherein the first scFv binds a first epitope of Tie-2; wherein the first scFv is covalently linked (directly or through a linker) to the N-terminal of an Fc fragment lacking a $CH_1$ domain; and, either (a) a second scFv fragment covalently linked to the C-terminal of the Fc fragment lacking the $CH_1$ domain (directly or through a linker), wherein the second scFv comprises three HCDRs (amino acids 541-549 (HCDR1), 567-573 (HCDR2), 612-626 (HCDR3) of SEQ ID NO:29) and three LCDRs (amino acids 679-684 (LCDR1), 702-704 (LCDR2), and 741-748 (LCDR3), and wherein the second scFv binds a second epitope of Tie-2; or, (b) an FD1 or FD2, or Tie-binding fragment thereof, that does not block binding of the first scFv to Tie-2; and wherein the first polypeptide dimerizes with a second polypeptide that is identical or substantially identical to the first polypeptide such that the first and the second polypeptide form a dimer.

In one embodiment, the Tie-binding protein comprises a first polypeptide comprising (a) a first scFv comprising three HCDRs (amino acids 58-66 (HCDR1), 84-90 (HCDR2), 129-137 (HCDR3) of SEQ ID NO:31) and three LCDRs (amino acids 196-201 (LCDR1), 219-221 (LCDR2), 258-264 (LCDR3) of SEQ ID NO:31), wherein the first scFv binds a first epitope of Tie-2; and wherein the first scFv is covalently linked (directly or through a linker) to the N-terminal of an Fc fragment lacking a $CH_1$ domain; and, (b) either (i) a second scFv fragment covalently linked to the C-terminal of the Fc fragment lacking the $CH_1$ domain (directly or through a linker), wherein the second scFv comprises three HCDRs (amino acids 58-65 (HCDR1), 83-90 (HCDR2), 129-139 (HCDR3) of SEQ ID NO:28) and three LCDRs (amino acids 192-201 (LCDR1), 219-221 (LCDR2), and 258-265 (LCDR3) of SEQ ID NO:28), and wherein the second scFv binds the second epitope of Tie-2; or, (ii) an FD1 or FD2, or Tie-binding fragment thereof, that does not block binding of the first scFv to Tie-2; and wherein the first polypeptide dimerizes with a second polypeptide that is identical or substantially identical to the first polypeptide such that the first and the second polypeptide form a dimer.

In one embodiment, the Tie-binding protein comprises, from N-terminal to C-terminal, a polypeptide that comprises (a) a first heavy chain variable domain ($V_H$) present within the span of amino acids 33-150 of SEQ ID NO:28; (b) a first light chain variable domain present within the span of amino acids 166-277 of SEQ ID NO:28; (c) a multimerizing component; (d) a second $V_H$ present within the span of amino acids 516-637 of SEQ ID NO:28; and, (e) a second $V_L$ present within the span of amino acids 653-762 of SEQ ID NO:28. In one embodiment, the multimerizing component is an immunoglobulin heavy chain constant domain (HC) or an HC that lacks a $CH_1$ domain. In a specific embodiment, the multimerizing component is an IgG heavy chain constant region that lacks a $CH_1$ domain. In a specific embodiment, the multimerizing component comprises amino acids 281-507 of SEQ ID NO:28. In one embodiment, the Tie-binding protein is a dimer of SEQ ID NO:28.

In one embodiment, framework (FR) regions of the first and/or the second scFv are human framework regions. In one embodiment, one or more of the recited CDRs are humanized. In a specific embodiment, the FR regions are human and one or more of the CDRs are humanized; in another embodiment the FR regions are human and all CDRs are humanized.

In one embodiment, a Tie-binding protein is provided that comprises a human antigen-binding domain that competes with the scFv of SEQ ID NO:30 for binding to Tie-2. In one embodiment, the human antigen-binding domain competes with the scFv contained within amino acids 33-277 of SEQ ID NO:28 for binding to Tie-2. In one embodiment, a Tie-binding protein is provided that comprises a human antigen-binding domain that binds the epitope of human Tie-2 which corresponds to the epitope on rTie-2 bound by either scFv of SEQ ID NO:30 or amino acids 33-277 of SEQ ID NO:28.

In one aspect, a Tie-binding protein comprising fusion polypeptide A-M-A' is provided, wherein: (a) A comprises a Tie-1-binding fragment of an antibody that binds a Tie-1 on the surface of a cell; (b) A' is selected from (i) an antibody fragment that binds a Tie-1, and (ii) a fibrinogen domain of Ang-1 (FD1) or Ang-2 (FD2), or Tie-1-binding fragment thereof; and (c) M is a multimerizing component; wherein binding of A to Tie-1 does not block binding of A' to Tie-1.

In one embodiment, the Tie-binding protein when exposed to a cell bearing a Tie-1, activates Tie-1 and Tie-1 is phosphorylated. In one embodiment, the Tie-binding protein when exposed to a cell bearing a Tie-2 activates the Tie-2 and Tie-2 is phosphorylated. In one embodiment, the phosphorylation is more than two-fold higher than occurs when the cell is exposed to a Tie-binding protein wherein A and A' block one another, as measured by immunoprecipitation of total Tie-1 and/or total Tie-2 and detecting phosphotyrosine. In another embodiment, the phosphorylation is more than four-fold. In another embodiment, more than ten-fold.

In one embodiment, the Tie-1-binding protein binds the Tie-1 receptor with higher affinity than FD1. In one embodiment, exposing a cell bearing a Tie-1 to the Tie-binding protein results in clustering of more than four Tie-1's (i.e., more than four Tie-1 receptors) of the cell and also results in phosphorylation and activation of Tie-1.

In one embodiment, the cell is a mammalian cell selected from a mouse, rat, hamster, monkey, ape, and human cell. In one embodiment, the Tie-1 is selected from mouse, rat, hamster, monkey, ape, and human Tie-1. In a specific embodiment, the Tie-1 is a human Tie-1.

In one embodiment, the Tie-binding protein comprises an A and/or an A' that is an scFv.

In one embodiment, A (or A') comprises FD1 or FD2, or a Tie-binding fragment thereof, that does not block binding of the scFv to Tie-1. In one embodiment, the FD1 comprises amino acids 515-728 of SEQ ID NO:30. In one embodiment, the FD2 comprises amino acids 515-727 of SEQ ID NO:31.

In one embodiment, M is selected from the group consisting of an Fc domain of IgG, and a polypeptide comprising a heavy chain $CH_2$ and $CH_3$ constant region. In one embodiment, M is an Fc domain of an IgG that lacks a $CH_1$ domain. In a specific embodiment, the Fc domain comprises amino acids 281-507 of SEQ ID NO:28.

In one embodiment, the Tie-binding protein comprises, from N-terminal to C-terminal, (a) a first Tie-1 binding region comprising a first scFv that comprises a CDR comprising a sequence selected from: amino acids 29-36 (HCDR1), 54-61 (HCDR2), 100-114 (HCDR3), 167-172 (LCDR1), 190-192 (LCDR2), 229-237 (LCDR3) of SEQ ID NO:50, wherein the Tie-binding protein binds a first epitope of Tie-1; (b) a multimerizing component; and, (c) a second Tie-binding region comprising either (i) a second scFv that comprises a CDR that binds a second epitope of Tie-1, or (ii) an FD1 or FD2, or Tie-binding fragment thereof. In one embodiment, the second scFv comprises three HCDRs and three LCDRs.

In one embodiment, the Tie-binding protein comprises, from N-terminal to C-terminal (a) a first Tie-1 binding region comprising a first scFv that comprises a CDR comprising a sequence selected from: amino acids 29-36 (HCDR1), 54-61 (HCDR2), 100-111 (HCDR3), 164-169 (LCDR1), 187-189 (LCDR2), 226-234 (LCDR3) of SEQ ID NO:51, wherein the Tie-binding protein binds a first epitope of Tie-1; (b) a multimerizing component; and, (c) a second Tie-binding region comprising either (i) a second scFv that comprises a CDR that binds a second epitope of Tie-1, or (ii) an FD1 or FD2, or Tie-binding fragment thereof. In one embodiment, the second scFv comprises three HCDRs and three LCDRs.

In one embodiment, the Tie-binding protein comprises a first polypeptide comprising first scFv comprising three HCDRs (amino acids 29-36 (HCDR1), 54-61 (HCDR2), 100-111 (HCDR3) of SEQ ID NO:51) and three LCDRs (amino acids 164-169 (LCDR1), 187-189 (LCDR2), 226-234 (LCDR3) of SEQ ID NO:51), wherein the first scFv that binds a first epitope of Tie-1; wherein the first scFv is covalently linked (directly or through a linker) to the N-terminal of an Fc fragment lacking a CH1 domain; and, either (a) a second scFv fragment covalently linked to the C-terminal of the Fc fragment lacking the CH1 domain (directly or through a linker), wherein the second scFv comprises three HCDRs (amino acids 509-516 (HCDR1), 534-541 (HCDR2), 580-594 (HCDR3) of SEQ ID NO:51) and three LCDRs (amino acids 647-652 (LCDR1), 670-672 (LCDR2), and 709-717 (LCDR3) of SEQ ID NO:51), wherein the second scFv binds a second epitope of Tie-1; or (b) an FD1 or FD2, or Tie-binding fragment thereof, that does not block binding of the first scFv to Tie-1; and wherein the first polypeptide dimerizes with a second polypeptide that is identical or substantially identical to the first polypeptide such that the first and the second polypeptide form a dimer.

In one embodiment, the Tie-binding protein comprises a first polypeptide comprising first scFv comprising three HCDRs (amino acids 29-36 (HCDR1), 54-61 (HCDR2), 100-114 (HCDR3) of SEQ ID NO:52) and three LCDRs (amino acids 167-172 (LCDR1), 190-192 (LCDR2), 229-237 (LCDR3) of SEQ ID NO:52), wherein the first scFv binds a first epitope of Tie-1; wherein the first scFv is covalently linked (directly or through a linker) to the N-terminal of an Fc fragment lacking a $CH_1$ domain; and, either (a) a second scFv fragment covalently linked to the C-terminal of the Fc fragment lacking the $CH_1$ domain (directly or through a linker), wherein the second scFv comprises three HCDRs (amino acids 29-36 (HCDR1), 54-61 (HCDR2), 100-111 (HCDR3) of SEQ ID NO:51) and three LCDRs (amino acids 164-169 (LCDR1), 187-189 (LCDR2), and 226-234 (LCDR3) of SEQ ID NO:51), wherein the second scFv binds a second epitope of Tie-1; or, (b) an FD1 or FD2, or Tie-binding fragment thereof, that does not block binding of the first scFv to Tie-1; and wherein the first polypeptide dimerizes with a second polypeptide that is identical or substantially identical to the first polypeptide such that the first and the second polypeptide form a dimer.

In one embodiment, the Tie-binding protein comprises, from N-terminal to C-terminal, a polypeptide that comprises (a) a first heavy chain variable domain ($V_H$) present within the span of amino acids 4-122 of SEQ ID NO:51; (b) a first light chain variable domain present within the span of amino acids 138-244 or 245 of SEQ ID NO:51; (c) a multimerizing component; (d) a second $V_H$ present within the span of amino acids 484-605 of SEQ ID NO:51; (e) a second $V_L$ present within the span of amino acids 621-728 of SEQ ID NO:51. In one embodiment, the multimerizing component is an immunoglobulin heavy chain constant domain (HC) or an HC that lacks a $CH_1$ domain. In a specific embodiment, the multimerizing component is an IgG that lacks a $CH_1$ domain. In one embodiment, the multimerizing component comprises amino acids 249-475 of SEQ ID NO:51). In a specific embodiment, the Tie-binding protein is a dimer of SEQ ID NO:51.

In one embodiment, framework (FR) regions of the first and/or the second scFv are human framework regions. In one embodiment, one or more of the recited CDRs are humanized. In a specific embodiment, the FR regions are human and one or more of the CDRs are humanized; in another embodiment the FR regions are human and all CDRs are humanized.

In one embodiment, a Tie-binding protein is provided that comprises a human antigen-binding domain that competes with the scFv of SEQ ID NO:50 for binding to Tie-1. In one embodiment, the human antigen-binding domain competes with the scFv contained within amino acids 4-245 of SEQ ID NO:51 for binding to Tie-1. In one embodiment, a Tie-binding protein is provided that comprises a human antigen-binding domain that binds the epitope of human Tie-1 which corresponds to the epitope on rTie-1 bound by either scFv of SEQ ID NO:50 or amino acids 4-245 of SEQ ID NO:51.

In one embodiment, a human or humanized Tie-binding protein is provided that comprises, from N-terminal to C-terminal, a human or humanized scFv that binds Tie-1, an Fc dimerizing sequence lacking a $CH_1$ domain, and an FD1 (or FD2), wherein the Tie-binding protein when exposed to a cell bearing a human Tie-1 and Tie-2 causes the human Tie-1 and the human Tie-2 to be phosphorylated, wherein the level of phosphorylation of the Tie-1 and/or Tie-2 as measured by a phosphotyrosine blot of immunoprecipitated total Tie-1 or total Tie-2 is at least two-fold, at least four-fold, or at least ten-fold higher than that caused by exposing the cell to a monospecific Tie-binding protein or to a mock (e.g., buffer control) treatment. In one embodiment, the human scFv binds human Tie-1 within a span of amino acids in the human Tie-1 sequence that corresponds, in an optimal alignment of human Tie-1 and rat Tie-1, with a span of amino acids that corresponds with the span of amino acids of rTie-1 within which the scFv of SEQ ID NO:52 binds rTie-1. In one embodiment, the span of amino acids is selected from four, six, eight, or ten amino acids. In one embodiment, the epitope bound on human Tie-1 by the human scFv is the corresponding epitope of rat Tie-1 with which the scFv of SEQ ID NO:52 binds.

In one aspect, a Tie-binding protein is provided, comprising a polypeptide that comprises, from N-terminal to C-terminal, (a) a first scFv that binds an epitope of a Tie receptor; (b) a multimerizing component; and, (c) a second scFv that binds the same epitope of the Tie receptor. In one embodiment, the multimerizing component comprises an immunoglobulin heavy chain constant region (HC), in another embodiment the multimerizing component comprises an HC that lacks a $CH_1$ domain. In one embodiment, the multimerizing component comprises amino acids 280-506 of SEQ ID NO:29.

In one embodiment, the Tie-binding protein binds a Tie-1 receptor. In one embodiment, the Tie-binding protein binds a Tie-2 receptor.

In one embodiment, the first scFv and the second scFv each comprise the same respective CDRs. In a specific embodiment, the first scFv and the second scFv are identical.

In one embodiment, the first scFv comprises three HCDRs (amino acids 58-66 (HCDR1), 84-90 (HCDR2), 129-143 (HCDR3) of SEQ ID NO:29) and three LCDRs (amino acids 196-201 (LCDR1), 219-221 (LCDR2), 258-265 (LCDR3) of SEQ ID NO:29).

In one embodiment, the first scFv comprises three HCDRs (amino acids 29-36 (HCDR1), 54-61 (HCDR2), 100-114 (HCDR3) of SEQ ID NO:50) and three LCDRs (amino acids 167-172 (LCDR1), 190-192 (LCDR2), and 229-237 (LCDR3) of SEQ ID NO:50).

In one aspect, a Tie-binding antibody is provided, wherein the Tie-binding antibody comprises (a) heavy chain CDR1 (amino acids 58-65), CDR2 (amino acids 83-90) and CDR3 (amino acids 129-139) of SEQ ID NO:28; (b) light chain CDR1 (amino acids 192-201), CDR2 (amino acids 219-221) and CDR3 (amino acids 258-265) of SEQ ID NO:28; and, (c) a light chain constant domain and a heavy chain constant region.

In one embodiment, the light chain constant domain and the heavy chain constant domain are human. In one embodiment, the human heavy chain constant domain is an IgG constant domain, in a specific embodiment, an $IgG_1$ constant domain. In one embodiment, the heavy chain and/or the light chain CDRs are humanized. In one embodiment, one or more of the framework regions (FRs) are human.

In one embodiment, the Tie-binding antibody comprises the heavy chain variable region present within the span of amino acids 33-150 of SEQ ID NO:28 and the light chain variable region present within the span of amino acids 166-277 of SEQ ID NO:28.

In one aspect, a Tie-binding antibody is provided, wherein the Tie-binding antibody comprises (a) heavy chain CDR1 (amino acids 58-66), CDR2 (amino acids 84-90) and CDR3 (amino acids 129-143) of SEQ ID NO:29; (b) light chain CDR1 (amino acids 196-201), CDR2 (amino acids 219-221) and CDR3 (amino acids 258-265) of SEQ ID NO:29; and, (c) a light chain constant domain and a heavy chain constant region.

In one embodiment, the light chain constant domain and the heavy chain constant domain are human. In one embodiment, the human heavy chain constant domain is an IgG constant domain, in a specific embodiment, an IgG1 constant domain. In one embodiment, the heavy chain and/or the light chain CDRs are humanized. In one embodiment, one or more of the framework regions (FRs) are human.

In one embodiment, the Tie-binding antibody comprises the heavy chain variable region present within the span of amino acids 33-154 of SEQ ID NO:29 and comprises the light chain variable region present within the span of amino acids 170-276 of SEQ ID NO:29.

In one aspect, a Tie-binding antibody is provided, wherein the Tie-binding antibody comprises (a) heavy chain CDR1 (amino acids 29-36), CDR2 (amino acids 54-61) and CDR3 (amino acids 100-114) of SEQ ID NO:50; (b) light chain CDR1 (amino acids 167-172), CDR2 (amino acids 190-192) and CDR3 (amino acids 229-237) of SEQ ID NO:50; and, (c) a light chain constant domain and a heavy chain constant region.

In one embodiment, the light chain constant domain and the heavy chain constant domain are human. In one embodiment, the human heavy chain constant domain is an IgG constant domain, in a specific embodiment, an IgG$_1$ constant domain. In one embodiment, the heavy chain and/or the light chain CDRs are humanized. In one embodiment, one or more of the framework regions (FRs) are human.

In one embodiment, the Tie-binding antibody comprises the heavy chain variable region present within the span of amino acids 4-125 of SEQ ID NO:50 and the light chain variable region present within the span of amino acids 141-248 of SEQ ID NO:50.

In one aspect, a Tie-binding antibody is provided, wherein the Tie-binding antibody comprises (a) heavy chain CDR1 (amino acids 29-36), CDR2 (amino acids 54-61) and CDR3 (amino acids 100-111) of SEQ ID NO:51; (b) light chain CDR1 (amino acids 164-169), CDR2 (amino acids 187-189) and CDR3 (amino acids 226-234) of SEQ ID NO:51; and, (c) a light chain constant domain and a heavy chain constant region sequence.

In one embodiment, the light chain constant domain and the heavy chain constant region are human. In one embodiment, the human heavy chain constant region is an IgG constant region, in a specific embodiment, an IgG$_1$ constant domain. In one embodiment, the heavy chain constant region is an IgG$_1$ constant region that lacks a CH$_1$. In one embodiment, the heavy chain and/or the light chain CDRs are humanized. In one embodiment, one or more of the framework regions (FRs) are human.

In one embodiment, the Tie-binding antibody comprises the heavy chain variable region present within the span of amino acids 4-122 of SEQ ID NO:51 and the light chain variable region present within the span of amino acids 138-244 or 245 of SEQ ID NO:51.

In one aspect, a method for activating a Tie-1 receptor (Tie-1) is provided, comprising exposing a cell that bears a Tie-1 to a Tie-1-binding protein, wherein the Tie-1-binding protein comprises a polypeptide that forms a dimer, wherein the polypeptide comprises, from N-terminal to C-terminal, (a) a first immunoglobulin heavy chain variable region ($V_H1$) and light chain variable region ($V_L1$) that binds a first epitope of Tie-1; (b) a multimerizing component; and, (c) either (i) a second immunoglobulin heavy chain variable region ($V_H2$) and light chain variable region ($V_L2$) that binds a second epitope of Tie-1, or (ii) an FD1 or FD2 domain; wherein binding of $V_H1$ and $V_L1$ does not block binding of $V_H2$ and $V_L2$, and does not block binding of FD1 and FD2.

In one embodiment, the Tie-1 is selected from a mouse, rat, hamster, monkey, ape, and human Tie-1.

In one aspect, a method for activating a Tie-2 receptor (Tie-2) is provided, comprising exposing a cell that bears a Tie-2 and bears a Tie-1 to a Tie-1-binding protein, wherein the Tie-1-binding protein comprises a polypeptide that forms a dimer, wherein the polypeptide comprises, from N-terminal to C-terminal, (a) a first immunoglobulin heavy chain variable region ($V_H1$) and light chain variable region ($V_L1$) that binds a first epitope of Tie-1; (b) a multimerizing component; and, (c) either (i) a second immunoglobulin heavy chain variable region ($V_H2$) and light chain variable region ($V_L2$) that binds a second epitope of Tie-1, or (ii) an FD1 or FD2 domain; wherein binding of $V_H1$ and $V_L1$ does not block binding of $V_H2$ and $V_L2$, and does not block binding of FD1 and FD2.

In one embodiment, the Tie-1 and Tie-2 are independently selected from a mouse, rat, hamster, monkey, ape, and human Tie. In one embodiment, the Tie-1 and the Tie-2 are human.

In one aspect, a method for activating a Tie-2 receptor (Tie-2) is provided, comprising exposing a cell that bears a Tie-2 to a Tie-2-binding protein, wherein the Tie-2-binding protein comprises a polypeptide that forms a dimer, wherein the polypeptide comprises, from N-terminal to C-terminal, (a) a first immunoglobulin heavy chain variable region ($V_H1$) and light chain variable region ($V_L1$) that binds a first epitope of Tie-2; (b) a multimerizing component; and, (c) either (i) a second immunoglobulin heavy chain variable region ($V_H2$) and light chain variable region ($V_L2$) that binds a second epitope of Tie-2, or (ii) an FD1 or FD2 domain; wherein binding of $V_H1$ and $V_L1$ does not block binding of $V_H2$ and $V_L2$, and does not block binding of FD1 and FD2.

In one embodiment, the Tie-2 is selected from a mouse, rat, hamster, monkey, ape, and human Tie. In one embodiment, the Tie-2 is human.

In one aspect, a method for activating a Tie-1 receptor (Tie-1) is provided, comprising exposing a cell that bears a Tie-1 to a Tie-2-binding protein, wherein the Tie-2-binding protein comprises a polypeptide that forms a dimer, wherein the polypeptide comprises, from N-terminal to C-terminal, (a) a first immunoglobulin heavy chain variable region ($V_H1$) and light chain variable region ($V_L1$) that binds a first epitope of Tie-2; (b) a multimerizing component; and, (c) either (i) a second immunoglobulin heavy chain variable region ($V_H2$) and light chain variable region ($V_L2$) that binds a second epitope of Tie-2, or (ii) an FD1 or FD2 domain; wherein binding of $V_H1$ and $V_L1$ does not block binding of $V_H2$ and $V_L2$, and does not block binding of FD1 and FD2.

In one embodiment, the Tie-1 and Tie-2 are independently selected from a mouse, rat, hamster, monkey, ape, and human Tie. In one embodiment, the Tie-1 and Tie-2 are human.

In one aspect, nucleic acids comprising Tie-binding sequences of the Tie-binding proteins are provided, as well as nucleic acids encoding the polypeptides of the Tie-binding proteins.

In another aspect, the invention features a vector comprising a nucleic acid sequence of the invention. The invention further features an expression vector comprising a nucleic acid of the invention, wherein the nucleic acid molecule is operably linked to an expression control sequence. Also provided is a host-vector system for the production of the fusion polypeptides of the invention which comprises the expression vector of the invention which has been introduced into a host cell or organism, including, but not limited to, transgenic animals, suitable for expression of the fusion polypeptides.

In another aspect, the invention features a method of producing a fusion polypeptide of the invention, comprising culturing a host cell transfected with a vector comprising a nucleic acid sequence of the invention, under conditions suitable for expression of the polypeptide from the host cell, and recovering the fusion polypeptide so produced.

In another aspect, the invention features therapeutic methods for the treatment of a target receptor-related disease or condition, comprising administering a therapeutically effective amount of an activating dimer of the invention to a subject in need thereof, wherein the target receptor is activated, and the disease or condition is ameliorated or inhibited.

Accordingly, in another aspect, the invention features pharmaceutical compositions comprising an activating dimer of the invention with a pharmaceutically acceptable carrier. Such pharmaceutical compositions may comprise dimeric proteins or nucleic acids which encode them.

In another aspect, a kit is provided that comprises one or more Tie-binding proteins of the invention. In one embodiment, the kit comprises a Tie-1-binding antibody. In one embodiment, the kit comprises a Tie-2-binding antibody. In one embodiment, the kit comprises a Tie-1-binding antibody and a Tie-2 binding antibody. In one embodiment, the one or more Tie-binding proteins is labelled. In one embodiment, the one or more Tie-binding proteins bind a Tie of an organism selected from a mouse, rat, hamster, monkey, ape, and a human.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Definitions

As used herein, the term "target receptor-related condition or disease" generally encompasses a condition of a mammalian host, particularly a human host, which is associated with a particular target receptor. Thus, treating a target receptor-related condition will encompass the treatment of a mammal, in particular, a human, who has symptoms reflective of decreased target receptor activation, or who is expected to have such decreased levels in response to a disease, condition or treatment regimen. Treating a target receptor-related condition or disease encompasses the treatment of a human subject wherein enhancing the activation of a target receptor with an activating dimer of the invention results in amelioration of an undesirable symptom resulting from the target receptor-related condition or disease. As used herein, an "target receptor-related condition" also includes a condition in which it is desirable to alter, either transiently, or long-term, activation of a particular target receptor.

Target Receptors

Examples of target receptors are members of the Eph family (e.g. EphA1, EphA2, EphA3, EphA4, EphA5, EphA6, EphA7, EphA8, EphB1, EphB2, EphB3, EphB4, EphB5, EphB6), Tie receptors (e.g. Tie-1 or Tie-2). Suitable ligands or fragments thereof include the soluble domain of an ephrin (e.g. ephrin-A1, ephrin-A2, ephrin-A3, ephrin-A4, ephrin-A5, ephrin-B1, ephrin-B2, ephrin-B3), and the fibrinogen domain of an angiopoietin (e.g. angiopoietin-1 (Ang1, Ang2, Ang3, Ang4).

Suitable target receptors are receptors that are activated when multimerized. This class of receptors includes, but is not limited to, those that possess an integral kinase domain. Within this class of integral kinase receptors are those that form homodimers, or clusters of the same receptor, such as Tie-1, Tie-2, EGFR, FGFR, the Trk family and the Eph family of receptors, and those that form heterodimers, or clusters, such as the VEGF receptors VEGFR1, VEGFR2, the PDGF receptors PDGFRα and PDGFRβ, and the TGF-β family receptors. Suitable target receptors also include, but are not limited to, the class of receptors with associated kinases. These receptors include those that form homodimers, or clusters, such as the growth hormone receptor, EPOR and the G-CSF receptor CD114, and those that form heterodimers, or clusters, such as the GM-CSF receptors GMRα and GMRβ.

Target Receptor-Specific Antibodies and Ligands

In specific embodiments, the activating dimers of the invention comprise one or more immunoglobulin binding domains isolated from antibodies generated against a selected target receptor. The term "immunoglobulin" or "antibody" as used herein refers to a mammalian, including human, polypeptide comprising a framework region from an immunoglobulin gene or fragments thereof that specifically binds and recognizes an antigen, which, in the case of the present invention, is a target receptor or portion thereof. If the intended activating dimer will be used as a human therapeutic, immunoglobulin binding regions should be derived from the corresponding human immunoglobulins or be a humanized immunoglobulin. The human immunoglobulin genes or gene fragments include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (eg. $IgG_1$, $IgG_2$, etc.). Typically, the antigen-binding region of an antibody will be the most critical in determining specificity and affinity of binding.

An exemplary immunoglobulin (antibody) structural unit of human IgG, comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" ($V_L$) and "variable heavy chain" ($V_H$) refer to these light and heavy chains respectively.

Antibodies exist as intact immunoglobulins, or as a number of well-characterized fragments produced by digestion with various peptidases, e.g., $F(ab)'_2$, Fab', etc. Thus, the terms immunoglobulin or antibody, as used herein, also includes antibody fragments either produced by the modification of whole antibodies, or those synthesized de novo using recombinant DNA methodologies (e.g., single chain Fv) (scFv) or those identified using phase display libraries (see, for example, McCafferty et al. (1990) Nature 348:552-554). In addition, the target receptor-binding domain component of the fusion polypeptides of the invention include the variable regions of the heavy ($V_H$) or the light ($V_L$) chains of immunoglobulins, as well as target receptor-binding portions thereof. Methods for producing such variable regions are described in Reiter, et al. (1999) J. Mol. Biol. 290:685-698.

Methods for preparing antibodies are known to the art. See, for example, Kohler & Milstein (1975) Nature 256: 495-497; Harlow & Lane (1988) Antibodies: a Laboratory Manual, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain or recombinant antibodies (U.S. Pat. Nos. 4,946,778; 4,816,567) can be adapted to produce antibodies used in the fusion polypeptides, activating dimers and methods of the instant invention. Also, transgenic mice, or other organisms such as other mammals, may be used to express human or humanized antibodies. Alternatively, phage display technology can be used to identify antibodies, antibody fragments, such as variable domains, and heteromeric Fab fragments that specifically bind to selected antigens. Phage display is of particular value to isolate weakly binding antibodies or fragments thereof from unimmunized animals which, when combined with other weak binders in accordance with the invention described herein, create strongly binding activating dimers.

Screening and selection of preferred immunoglobulins (antibodies) can be conducted by a variety of methods known to the art. Initial screening for the presence of monoclonal antibodies specific to a target receptor may be conducted through the use of ELISA-based methods or phage display, for example. A secondary screen is preferably conducted to identify and select a desired monoclonal antibody for use in construction of the fusion polypeptides of the invention. Secondary screening may be conducted with any suitable method known to the art.

Nucleic Acid Construction and Expression

Individual components of the fusion polypeptides of the invention may be produced from nucleic acids molecules using molecular biological methods known to the art. Nucleic acid molecules are inserted into a vector that is able to express the fusion polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion polypeptides of the invention under control of transcriptional/translational control signals. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art.

Immunoglobulin-derived components. The nucleic acid constructs include regions which encode binding domains derived from an anti-target receptor antibodies. In general, such binding domains will be derived from $V_H$ or $V_L$ chain variable regions. After identification and selection of antibodies exhibiting the desired binding characteristics, the variable regions of the heavy chains and/or light chains of each antibody is isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids.

The invention encompasses antibodies or antibody fragments which are humanized or chimeric. "Humanized" or chimeric forms of non-human (e.g., murine) antibodies are immunoglobulins, immunoglobulin chains or fragments thereof (such as Fv, Fab, Fab', F(ab') 2 or other antigen-binding subsequences of antibodies) that contain minimal sequences required for antigen binding derived from non-human immunoglobulin. They have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $IgG_1$ and $IgG_4$. Human isotype $IgG_1$ is preferred. A typical chimeric antibody is thus a hybrid protein consisting of the V or antigen-binding domain from a mouse antibody and the C or effector domain from a human antibody. Humanized antibodies have variable region framework residues substantially from a human antibody (termed an acceptor antibody) and complementarity determining regions (CDR regions) substantially from a mouse antibody, (referred to as the donor immunoglobulin). See, Queen et al., Proc. Natl. Acad Sci. USA 86:10029-10033 (1989) and WO 90/07861, U.S. Pat. Nos. 5,693,762, 5,693,761, 5,585,089, 5,530,101 and 5,225,539. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly; (2) is adjacent to a CDR region; (3) otherwise interacts with a CDR region (e.g. is within about 6 Å of a CDR region), or (4) participates in the $V_L$-$V_H$ interface. Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Fully human antibodies may be made by any method known to the art. For example, U.S. Pat. No. 6,596,541 describes a method of generating fully human antibodies. Briefly, initially a transgenic animal such as a mouse is generated that produces hybrid antibodies containing human variable regions (VDJ/VJ) and mouse constant regions. This is accomplished by a direct, in situ replacement of the mouse variable region (VDJ/VJ) genes with their human counterparts. The mouse is then exposed to human antigen, or an immunogenic fragment thereof. The resultant hybrid immunoglobulin loci will undergo the natural process of rearrangements during B-cell development to produce hybrid antibodies having the desired specificity. The antibody of the invention is selected as described above. Subsequently, fully-human antibodies are made by replacing the mouse constant regions with the desired human counterparts. Fully human antibodies can also be isolated from mice or other transgenic animals such as cows that express human transgenes or minichromosomes for the heavy and light chain loci. (Green (1999) J Immunol Methods. 231:11-23 and Ishida et al (2002) Cloning Stem Cells. 4:91-102). Fully human antibodies can also be isolated from humans to whom the protein has been administered. Fully human antibodies can also be isolated from immune compromised mice whose immune systems have been regenerated by engraftment with human stem cells, splenocytes, or peripheral blood cells (Chamat et al (1999) J Infect Dis. 180:268-77). To enhance the immune response to the protein of interest one can knockout the gene encoding the protein of interest in the human-antibody-transgenic animal.

Receptor-binding domains. In accordance with the invention, the nucleic acid constructs include components which encode binding domains derived from target receptor ligands. After identification of a ligand's target receptor-binding domain exhibiting desired binding characteristics, the nucleic acid that encodes such domain is used in the nucleic acid constructs. Such nucleic acids may be modified, including additions of nucleotide sequences encoding amino acids and/or carrying restriction sites, deletions of nucleotide sequences encoding amino acids, or substitutions of nucleotide sequences encoding amino acids.

The nucleic acid constructs of the invention are inserted into an expression vector or viral vector by methods known to the art, wherein the nucleic acid molecule is operatively linked to an expression control sequence. Also provided is a host-vector system for the production of the fusion polypeptides and activating dimers of the invention, which comprises the expression vector of the invention, which has been introduced into a suitable host cell. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

The invention further encompasses methods for producing the activating dimers of the invention by growing cells transformed with an expression vector under conditions permitting production of the fusion polypeptides and recovery of the activating dimers formed from the fusion polypeptides. Cells may also be transduced with a recombinant virus comprising the nucleic acid construct of the invention.

The activating dimers may be purified by any technique which allows for the subsequent formation of a stable dimer. For example, and not by way of limitation, the activating dimers may be recovered from cells either as soluble polypeptides or as inclusion bodies, from which they may be extracted quantitatively by 8M guanidinium hydrochloride and dialysis. In order to further purify the activating dimers, conventional ion exchange chromatography, hydrophobic interaction chromatography, reverse phase chromatography or gel filtration may be used. The activating dimers may also be recovered from conditioned media following secretion from eukaryotic or prokaryotic cells.

Screening and Detection Methods

The activating dimers of the invention may also be used in in vitro or in vivo screening methods where it is desirable to detect and/or measure target receptor levels. Screening methods are well known to the art and include cell-free, cell-based, and animal assays. In vitro assays can be either solid state or soluble. Target receptor detection may be achieved in a number of ways known to the art, including the use of a label or detectable group capable of identifying an activating dimer which is bound to a target receptor. Detectable labels are well developed in the field of immunoassays and may generally be used in conjunction with assays using the activating dimer of the invention.

Therapeutic Methods

The ability of the activating dimers of the invention to exhibit high affinity binding for their receptors makes them therapeutically useful for efficiently activating their receptors. Thus, it certain instances it may be to increase the effect of endogenous ligands for target receptors, such as, for example, the ephrins. For example, in the area of nervous system trauma, certain conditions may benefit from an increase in ephrin responsiveness. It may therefore be beneficial to increase the binding affinity of an ephrin in patients suffering from such conditions through the use of the compositions described herein.

The invention herein further provides for the development of an activating dimer described herein as a therapeutic for the treatment of patients suffering from disorders involving cells, tissues or organs which express the Tie-2 receptor. Such molecules may be used in a method of treatment of the human or animal body, or in a method of diagnosis.

The target receptor known as Tie-2 receptor has been identified in association with endothelial cells and, as was previously demonstrated, blocking of agonists of the receptor such as Tie-2 ligand 1 (Ang1) has been shown to prevent vascularization. Accordingly, activating dimers of the invention wherein the target receptor is Tie-2 may be useful for the induction of vascularization in diseases or disorders where such vascularization is indicated. Such diseases or disorders would include wound healing, ischemia and diabetes. The ligands may be tested in animal models and used therapeutically as described for other agents, such as vascular endothelial growth factor (VEGF), another endothelial cell-specific factor that is angiogenic. Ferrara et al. U.S. Pat. No. 5,332,671 issued Jul. 26, 1994. Ferrara et al. describe in vitro and in vivo studies that may be used to demonstrate the effect of an angiogenic factor in enhancing blood flow to ischemic myocardium, enhancing wound healing, and in other therapeutic settings wherein neoangiogenesis is desired. According to the invention, such a Tie-2 specific activating dimer may be used alone or in combination with one or more additional pharmaceutically active compounds such as, for example, VEGF or basic fibroblast growth factor (bFGF).

Methods of Administration

Methods known in the art for the therapeutic delivery of agents such as proteins or nucleic acids can be used for the therapeutic delivery of an activating dimer or a nucleic acid encoding an activating dimer of the invention for activating target receptors in a subject, e.g., cellular transfection, gene therapy, direct administration with a delivery vehicle or pharmaceutically acceptable carrier, indirect delivery by providing recombinant cells comprising a nucleic acid encoding an activating dimer of the invention.

Various delivery systems are known and can be used to administer the activating dimer of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, pulmonary, intranasal, intraocular, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

Pharmaceutical Compositions

The present invention also provides pharmaceutical compositions comprising an activating dimer of the invention and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. (See, for example, "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Kits

The invention also provides a pack or kit (e.g., a pharmaceutical pack or kit) comprising one or more containers filled with at least one activating dimer of the invention. The kits of the invention may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Transgenic Animals

The invention includes transgenic non-human animals expressing a fusion polypeptide of the invention. A transgenic animal can be produced by introducing nucleic acid into the male pronuclei of a fertilized oocyte, e.g., by microinjection, retroviral infection, and allowing the oocyte to develop in a pseudopregnant female foster animal. Any of the regulatory or other sequences useful in expression vectors can form part of the transgenic sequence. A tissue-specific regulatory sequence(s) can be operably linked to the transgene to direct expression of the transgene to particular cells. A transgenic non-human animal expressing an fusion polypeptide of the invention is useful in a variety of applications, including as a means of producing such fusion proteins Further, the transgene may be placed under the control of an inducible promoter such that expression of the fusion polypeptide may be controlled by, for example, administration of a small molecule.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Production of Anti-Tie-2 Hybridomas

Five 8-weeks old Balb/c mice were first immunized with purified human Tie-2-Fc (hTie-2-Fc); each mouse was injected subcutaneously with 200 µl emulsion containing 100 µg purified hTie-2-Fc protein and 100 µl Freund's complete adjuvant. Fifteen days after the primary injection, each mouse received subcutaneous injection of 200 µl emulsion containing 100 µg purified hTie-2-Fc in 100 µl PBS and 100 µl Freund's incomplete adjuvant. This injection was repeated for the five mice seven days later. One mouse was used for generation of hybridomas against hTie-2. Each of the four remaining mice were given subcutaneous injections of 200 µl emulsion each containing 100 µg purified rat Tie-2-Fc (rTie-2-Fc) in 100 µl PBS and 100 µl Freund's incomplete adjuvant six months after the primary injection of hTie-2-Fc. Eleven days later, the immune response of the mice to rTie-2-Fc was boosted by subcutaneous injection of 200 µl of emulsion containing 100 µg purified rTie-2-Fc in 100 µl PBS and 100 µl Freund's incomplete adjuvant for each mouse. Mouse sera were collected from tail veins three days after the injection, then the antibody titers against rTie-2-Fc were determined by ELISA. The two mice with the highest titers were given a final boost by tail vein injection of 100 µg purified rTie-2-Fc in 100 µl PBS. The mice were sacrificed three days later and their spleen cells were collected for fusion with Sp2/0-Ag14 cells.

To generate hybridomas, mouse spleen cells were fused with Sp2/0-Ag14 myeloma cells using polyethylene glycol (PEG). Briefly, after the spleens were aseptically removed from the mice, one tip of each spleen was cut open and spleen cells collected. The spleen cells were washed twice with D-MEM and cell numbers were counted using a hemocytometer. $2 \times 10^8$ spleen cells were combined with $3 \times 10^7$ Sp2/0-Ag14 cells that were in log growth stage. The cell mix was washed with 30 mls D-MEM. 1 ml 50% PEG at 37° C. was slowly added to the cell pellet while stirring. D-MEM was added to the mix to bring the volume to 10 mls. The cells were spun down at 400× g for 10 minutes. After removal of supernatant, the cells were gently resuspended in 20 mls growth medium containing 60% D-MEM with 4.5 g/L glucose, 20% FCS, 10% NCTC109 medium, 10% hybridoma cloning factor, 1 mM oxaloacetate, 2 mM glutamine, 0.2 units/ml insulin, and 3 µM glycine. The cells were transferred to two T225 flasks, each containing 100 mls of the growth medium and were put into a tissue culture incubator. On the next day, 1×HAT was added to the medium to select against the myeloma cells that were not fused. Nine days after the fusion, the cultures were replenished with fresh medium. Human IgG was added to the cultures at 1 mg/ml. On the tenth day after the fusion, $2.6 \times 10^7$ fused cells were stained sequentially with 1 µg/ml biotin-rTie-2-Fc for one hour and 2.5 µg/ml phycoerythrin (PE)-conjugated streptavidin for 45 minutes in growth medium at room temperature. As a control, $1 \times 10^6$ fused cells were stained with 2.5 µg/ml PE-streptavidin for 45 minutes at room temperature. The cells were washed with 10 ml PBS after each stain. After staining, the cells were resuspended in PBS with 0.1% FCS and were analyzed by flow cytometry on a MoFlo (Cytomation). A population of cells (4% total cells) stained with both biotin rTie-2-Fc and PE-streptavidin exhibited fluorescence higher than the unstained cells and the cells stained with PE-streptavidin alone. The cells in this 4% gate were cloned by sorting single cells into two 96-well plates containing 200 µl growth medium per well. The cells were cultured for 10 days before splitting into two sets of 96-well plates. Cells in one set of plate were processed for RT-PCR of mouse IgG heavy chain variable region following by sequencing. The clones were grouped into 14 bins, with members of each bin having identical sequence in their heavy chain variable region. Conditioned medium of hybridoma cells in each bin was tested for its ability to stimulate phosphorylation of rTie-2 in cultured rat aortic endothelial cells (RAECs).

Antibodies from two hybridomas, B2 and A12A, were chosen for further study because they were active in phosphorylation of Tie-2 in RAECs, and did not compete for binding to rTie-2 as determined by BIAcore analysis. In addition, these antibodies did not block binding of derivatives of angiopoietin-1 (Ang1) and angiopoietin-2 (Ang2), the natural ligands of Tie-2.

Example 2

Construction of scFvs (B2 and A12A)

Generally, antibody variable regions from hybridomas expressing antibodies specific for rTie-2 were cloned by first determining the sequence of RT-PCR products using primers specific for mouse antibody variable regions, then using specific primers based on the determined sequence in order to amplify DNA fragments encoding scFvs. The scFv DNA fragments were cloned such that they could be cassette exchanged with multiple plasmids to yield all combinations of activating dimers. For example, one amplified scFv fragment could be fused to a signal sequence at the N-terminus and to a coding sequence for the IgG Fc domain at the C-terminus, or it could be fused to the C-terminus of an IgG Fc coding sequence such that the 3' end of the scFv coding sequence contained a translation stop codon.

The B2 hybridoma was found to express an antibody capable of inducing phosphorylation of the Tie-2 receptor in RAECs. Total RNA was isolated from this hybridoma using the promega SV96 Total RNA Isolation System (Promega) and variable heavy cDNA was synthesized using the Qiagen One-Step RT-PCR system (Qiagen) with heavy chain primers from the Ratner primer set (Wang et al. (2000) J. Immunol. Methods 233:167) that included equimolar amounts of the 5' primers (SEQ ID NO:1-7) and the 3' primer (SEQ ID NO:8). Similarly, the light chain variable regions were amplified from cDNA using equimolar amounts of the light chain-specific primers (SEQ ID NO:9 and 10). The amplified variable region fragments were cloned into the pCR2.1-TOPO vector (Invitrogen) and the DNA sequences were determined. Based on the determined variable region sequences for the B2 antibody, the variable heavy sequence was PCR amplified using the pCR2.1-TOPO cloned variable region as template and an equimolar mix of 5' and 3' primers (SEQ ID NO: 19 and SEQ ID NO: 20). The variable light sequence was PCR amplified using a similar strategy. The pCR2.1-TOPO cloned variable region was used as template and an equimolar mix of 5' and 3' primers (SEQ ID NO:21 and SEQ ID NO:22). The variable regions were joined by a (G4S)3 linker; scFv genes were assembled and PCR amplified using an equimolar mix of the above specific variable heavy and variable light PCR products and an equimolar mix of 5' B2 heavy primer (SEQ ID NO:19) and the 3' light primer (SEQ ID NO:22). PCR product was cloned into Invitrogen pCR2.1-TOPO (Invitrogen) to yield pRG1039. The sequence was confirmed before sub-cloning the 744bp AscI/SrfI to fuse the scFv gene to the N-terminus of a DNA encoding the human IgG1 Fc fragment (hFc), or the 753bp AscI/NotI restriction fragments to fuse the same scFv to the C-terminus of a DNA encoding hFc.

The A12A hybridoma was also found to express an antibody capable of inducing phosphorylation of the Tie-2 receptor in RAECs. Total RNA was isolated from this hybridoma using the Quick Prep mRNA purification kit (Amersham Pharmacia Biotech) and variable heavy cDNA was synthesized using the Qiagen One-Step RT-PCR system, with equimolar amounts of primers from the from the Wright primer set (Morrison et al. (1995) Antibody Engineering, second edition, Borrebaeck, C. K. A. editor 267-293) that included the 5' heavy chain primers (SEQ ID NO:11-13) and the 3' primer (SEQ ID NO:8). Similarly, the light chain variable regions were amplified from cDNA with equimolar amounts of the 5' heavy chain primers (SEQ ID NO:14-18) and the 3' primer (SEQ ID NO:10). The amplified variable region fragments were cloned into the pCR2.1-TOPO vector (Invitrogen) and the DNA sequences were determined.

Based on the determined variable region sequences for the A12A antibody, the variable heavy sequence was PCR amplified using the pCR2.1-TOPO cloned variable region as template and an equimolar mix of 5' and 3' primers (SEQ ID NO:23 and SEQ ID NO:24). The variable light sequence was PCR amplified using a similar strategy. The pCR2.1-TOPO cloned variable region was used as template and an equimolar mix of 5' and 3' primers (SEQ ID NO:25 and SEQ ID NO:26). The variable regions were joined by a $(G_4S)_3$ linker; scFv genes were assembled and PCR amplified using an equimolar mix of the above specific variable heavy and variable light PCR products and an equimolar mix of 5' A12A heavy primer (SEQ ID NO:23) and the 3' light primer (SEQ ID NO:26). PCR product was cloned into Invitrogen pCR2.1-TOPO to yield pRG1090. The sequence was confirmed before sub-cloning the 747bp Ascl/Srfl to fuse the scFv gene to the N-terminus of a DNA encoding the hFc fragment.

Example 3

Construction of Monospecific and Bispecific Activating Dimers

The general scheme for constructing both monspecific and bispecific tetravalent activating dimers was based on the ability of either the B2 or A12A scFv genes to be inserted between the murine ROR1 signal sequence (SEQ ID NO:27) and the gene encoding hFc (nucleotides 85 to 765 of GenBank accession # X70421) when cut with one set of restriction enzymes, or after the hFc gene if cut with a different set of enzymes. This design of the scFv genes allowed the exchange of scFv cassettes among plasmids to obtain different combinations of scFv and hFc using standard known methods. All constructs have an optional three amino acid linker (spacer) between the cleavage site of the signal peptide and the start of the scFv gene, resulting from engineering a restriction site onto the 5' end of the scFv genes. Similarly, fusion to the amino terminus of the hFc gene was facilitated by a three amino acid sequence (Gly-Pro-Gly), and fusion to the carboxy terminus of the hFc gene was facilitated by an eight amino acid sequence consisting of the residues $Gly_4$-Ser-Gly-Ala-Pro (SEQ ID NO:32) As a consequence of the terminal restriction site linkers on the scFv genes, all constructs that have a carboxy terminal scFv end with the amino acids Gly-Pro-Gly.

Two types of svFc-based chimeric molecules were constructed to assess the ability of scFv-based molecules to activate the rTie-2 receptor. One type of molecule used a single scFv fused to both the N-terminus and the C-terminus of hFc, the consequence of which was a monospecific tetravalent molecule capable of binding rTie-2. This molecule was expected to be capable of simultaneously binding four rTie-2 molecules. The plasmid pTE586 encodes the gene for $scFv_{B2}$-Fc-$scFv_{B2}$ (SEQ ID NO: 29) whose secretion is directed by the mROR1 signal peptide. The expression of $scFv_{B2}$-Fc-$scFv_{B2}$ in pTE586 was directed by the CMV-MIE promoter when transfected into CHO cells. This protein was easily purified by Protein A-Sepaharose affinity chromatography.

Construction of an scFv-Fc-scFv molecule wherein the two scFv domains are derived from two different non-competing anti-rTie-2 antibodies would yield a molecule capable of clustering more than four receptors, in contrast to the $scFv_{B2}$-Fc-$scFv_{B2}$ described above, which can cluster only four receptors. It was determined by BIAcore analysis that the binding of the B2 antibody did not block binding of A12A to rTie-2, and A12A binding first did not block binding of B2. Consequently, scFv molecules made from these antibodies should be capable of clustering more than four receptors. To construct a bispecific tetravalent scFv-based molecule, the $scFv_{A12A}$ gene was used in combination with the $scFv_{B2}$ gene to yield $scFv_{A12A}$-Fc-$scFv_{B2}$ (SEQ ID NO: 28). The plasmid pTE585 encodes the gene for $scFv_{A12A}$-Fc-$scFv_{B2}$ and has the mROR1 signal peptide and CMV-MIE promoter when transfected into CHO cells. Both $scFv_{B2}$-Fc-$scFv_{B2}$ and $scFv_{A12A}$-Fc-$scFv_{B2}$ were expressed in CHO cells, and purified by Protein A-Sepharose affinity chromatography.

Example 4

Assays

Antibodies to rTie-2, and chimeric molecules related to these antibodies, were evaluated for their ability to induce phosphorylation of Tie-2 in cultured rat aortic endothelial cells. Confluent RAECs, between passage 3 and 6 (Vec Technologies), were grown in MCDB-131 media (Vec Technologies) on 0.2% gelatin coated T-75 flasks. Cells were starved for 2 hrs. in serum-free DME-Hi glucose medium (Irvine Scientific) prior to incubation at 37° C. for 5 min. in 1.5 ml serum-free DME-Hi glucose medium with 0.1% BSA and the challenge molecule. The challenge medium was then removed and cells were lysed in 20 mM Tris, pH 7.6, 150 mMNaCl, 50 mM NaF, 1 mM Na orthovanadate, 5 mM benzamidine, 1mM EDTA, 1% NP-40, 0.5% sodium deoxycholate, 0.1% SDS, with 10 µg/ml leupeptin, 10 µg/ml aprotinin, and 1 mM PMSF. Tie-2 was immunoprecipitated by incubating the lysates at 4° C. for 16 hrs. with 5 µg anti-Tie-2 mouse monoclonal antibody KP-m33, 10 µg biotinylated anti-mouse IgG (Jackson Laboratories), and 100 µl of neutravidin beads (Pierce). Beads were collected by centrifugation, washed 3 times with RIPA buffer, and bound proteins were eluted with 40 µl of 5× Laemmli buffer with 10% B-mercaptoethanol by heating at 100° C. for 5 min. After SDS-gel electrophoresis on a 4-12% Tris/glycine polyacrylamide gel (Novex), proteins were transferred to PVDF membranes and probed with mouse anti-phophotyrosine monoclonal antibody 4G10 (Upstate) then detected using goat anti-mouse IgG-HRP conjugate (Pierce) followed by ECL reagent (Amersham). The ability to induce Tie-2 phosphorylation in RAECs was determined for each activating dimer. Activity was evaluated by comparison to the level of stimulation obtained with FD1-Fc-FD1 (BA1)—a chimeric protein shown to be as active as Ang1 in binding and activation Tie-2 (Davis et al. (2003) Nature Struct. Biol. 10:38-44) (FD1 or FD2=human fibrinogen domain of Ang1 or Ang2, respectively). Maximum stimulation (ECmax) of Tie-2 in RAECs was observed when BA1 was used at about 0.5 to 1.0µg/ml, and phosphorylation levels in mock treated cells were low. Similarly, the ECmax of $scFv_{B2}$-Fc-$scFv_{B2}$, $scFv_{A12A}$-Fc-$scFv_{B2}$, $scFv_{B2}$-Fc-FD1, and $scFv_{B2}$-Fc-FD2 were about 0.5 to 1.0 µg/ml. In all cases, the scFv-based molecules were capable of inducing a higher phosphorylation signal than observed for the related native antibodies isolated from hybridoma conditioned media.

Purified scFv$_{B2}$-Fc-scFv$_{B2}$ and scFv$_{A12.4}$-Fc-scFv$_{B2}$ were characterized for their ability to bind rTie-2 and induce phosphorylation. Binding to rTie-2 was determined by BIAcore analysis. Both the monospecific and the bispecific activating dimers were found to have significantly higher affinity for rTie-2 than FD1-Fc-FD1. In addition, both scFv$_{B2}$-Fc-scFv$_{B2}$ and scFv$_{A12.4}$-Fc-scFv$_{B2}$ were able to stimulate phosphorylation of rTie-2 in RAECs comparable to FD1-Fc-FD1.

Example 5

Construction of scFv/Ligand Activating Dimers

Bispecific tetravalent molecules were constructed to include both Tie-2 specific scFv and FD1 or FD2. The chimeric molecules were made by fusing the gene encoding scFv$_{B2}$ to the N-terminus of hFc and the gene encoding Ang1 FD (Phe283 to Phe498 of GenBank accession # Q15389) or Ang2 FD (Phe281 to Phe496 of GenBank accession # O15123) to the C-terminus. Plasmid pTE514 encodes the gene for scFv$_{B2}$-Fc-FD1 (SEQ ID NO: 30) and contained the mROR1 signal peptide and CMV-MIE promoter. Plasmid pTE614 encodes the gene for scFv$_{B2}$-Fc-FD2 (SEQ ID NO: 31) and contained the mROR1 signal peptide and CMV-MIE promoter. Similar to scFv$_{B2}$-Fc-scFv$_{B2}$ and scFv$_{A12.4}$-Fc-scFv$_{B2}$ the proteins expressed from pTE514 and pTE614 had a Gly-Ala-Pro linker between the mROR1 signal peptide and the scFv$_{B2}$, a Gly-Pro-Gly linker between the N-terminal scFv$_{B2}$ and hFc and a Gly$_4$-Ser-Gly-Ala-Pro linker (SEQ ID NO:32) between the C-terminus of hFc and the N-terminus of the Ang FDs. Both scFv$_{B2}$-Fc-FD1 and scFv$_{B2}$-Fc-FD2 were expressed and purified as described above.

Purified scFv$_{B2}$-Fc-FD1 and scFv$_{B2}$-Fc-FD2 were characterized for their ability to bind rTie-2 and induce phosphorylation as described in above. As determined by BIAcore analysis, the chimeric activating dimer scFv$_{B2}$-Fc-FD1 was found to have significantly higher affinity for rTie-2 (0.04 nM) than FD1-Fc-FD1 (2 nM). Moreover, both scFv$_{B2}$-Fc-FD1 and scFv$_{B2}$-Fc-FD2 were able to stimulate phosphorylation of rTie-2 in RAECs comparable to FD1-Fc-FD1.

Example 6

Construction of Fully Human Activating Dimers

Bispecific tetravalent molecules are formed from dimerized fusion constructs of the invention which include either two scFvs derived from human antibodies specific for hTie-2 or one scFv derived from a human antibody specific for hTie-2 and human FD1 or FD2. Human scFvs specific for hTie-2 are obtained by methods known to the art and as described above. In one embodiment, human scFvs are obtained recombinantly as described in Reiter et al. (1999) J. Mol. Biol. 290:685-698 and Gilliland et al. (1996) Tissue Antigens 47(1):1-20.

Example 7

Construction of scFvs (1-1F11 and 2-1G3)

Anti-rTie-1 hybridomas were produced following the procedures described above for the production of anti-rTie-2 hybridomas. Briefly, mice were immunized three times with purified rat Tie-1-Fc protein and Freund's adjuvant. Spleen cells from the mouse with the highest anti-Tie-1 antibody titer were fused with Sp2/0-Ag14 myeloma cells using polyethylene glycol (PEG). After fusion, the cells were cultured in two T225 flasks. HAT was added to the cultures on the next day. Nine days after the fusion, the cultures were replenished with fresh medium. Human IgG was added to the cultures at 1 mg/ml. On the tenth day after the fusion, the HAT-resistant cells were stained sequentially with 1 µg/ml biotin-rat Tie-1-Fc for one hour and 2.5 µg/ml phycoerythrin (PE)-conjugated streptavidin for 45 minutes in growth medium at room temperature. After staining, the cells were analyzed by flow cytometery. Cells that bound rTie-1-Fc were cloned by sorting single cells into 96-well plates. The 96-well plate cultures were split into two sets ten days after sorting. RT-PCR of mouse IgG heavy chain variable region followed by sequencing were performed on one set of the 96-well plate cultures. Clones with unique IgG heavy chain variable region sequences were identified and expanded for the production of anti-rTie-1 antibodies. Antibodies were tested for binding rTie-1 protein and two clones, 1-1F11 and 1-2G3, were chosen for more detailed study.

The 1-1F11 hybridoma was found to express an antibody capable of inducing phosphorylation of the Tie-1 receptor in RAECs. Messenger RNA was isolated and variable heavy cDNA synthesized as described above with heavy chain primers from the Wright primer set (Morrison et al. (1995) Antibody Engineering, second edition, Borrebaeck, C. K. A. editor 267-293) that included the 5' heavy chain primers (SEQ ID NO:35-37) and the 3' primer (SEQ ID NO:33). Similarly, the light chain variable regions were amplified from cDNA with equimolar amounts of the 5' light chain primers (SEQ ID NO:38-41) and the 3' primer (SEQ ID NO:34). The amplified variable region fragments were cloned into the pCR2.1-TOPO vector (Invitrogen) and DNA sequences determined. Based on the determined variable region sequences for the 1-1F11 antibody, the variable heavy sequence was PCR amplified using the pCR2.1-TOPO cloned variable region as template and an equimolar mix of 5' and 3' primers (SEQ ID NO:42 and SEQ ID NO:43). The variable light sequence was PCR amplified using a similar strategy. The pCR2.1-TOPO cloned variable region was used as template and an equimolar mix of 5' and 3' primers (SEQ ID NO:44 and SEQ ID NO:45). The variable regions were joined by a (G$_4$S)$_3$ linker; scFv genes were assembled and PCR amplified using an equimolar mix of the above specific variable heavy and variable light PCR products and an equimolar mix of 5' heavy primer (SEQ ID NO:42) and the 3' light primer (SEQ ID NO:45). PCR product was cloned into Invitrogen pCR2.1-TOPO (Invitrogen) to yield pRG1192. The sequence was confirmed before sub-cloning the 747 bp Ascl/Srfl to fuse the scFv gene to the N-terminus of a DNA encoding the human IgG$_1$ Fc fragment (hFc), or the 756 bp Ascl/Notl restriction fragments to fuse the same scFv to the C-terminus of a DNA encoding hFc.

The 2-1G3 hybridoma was also found to express an antibody capable of inducing phosphorylation of the Tie-1 receptor in RAECs. Messenger RNA was isolated and variable heavy cDNA synthesized as described above with equimolar amounts of primers from the from the Wright primer set (Morrison et al. (1995) supra) that included the 5' heavy chain primers (SEQ ID NO:35-37) and the 3' primer (SEQ ID NO:33). Similarly, the light chain variable regions were amplified from cDNA with equimolar amounts of the 5' heavy chain primers (SEQ ID NO:38-41) and the 3' primer (SEQ ID NO:34). The amplified variable region fragments were cloned into the pCR2.1-TOPO vector (Invitrogen) and the DNA sequences were determined.

Based on the determined variable region sequences for the 2-1G3 antibody, the variable heavy sequence was PCR amplified using the pCR2.1-TOPO cloned variable region as template and an equimolar mix of 5' and 3' primers (SEQ ID NO:46 and SEQ ID NO:47). The variable light sequence was PCR amplified using a similar strategy. The pCR2.1-TOPO cloned variable region was used as template and an equimolar mix of 5' and 3' primers (SEQ ID NO:48 and SEQ ID NO:49). The variable regions were joined by a $(G_4S)_3$ linker; scFv genes were assembled and PCR amplified using an equimolar mix of the above specific variable heavy and variable light PCR products and an equimolar mix of 5' 2-1G3 heavy primer (SEQ ID NO:46) and the 3' light primer (SEQ ID NO:49). PCR product was cloned into Invitrogen pCR2.1-TOPO (Invitrogen) to yield pRG1198. The sequence was confirmed before sub-cloning the 738 bp Ascl/Srfl to fuse the scFv gene to the N-terminus of a DNA encoding the hFc fragment or the 747 bp Ascl/Notl restriction fragments to fuse the same scFv to the C-terminus of a DNA encoding hFc.

Example 8

Construction of Monospecific and Bispecific Activating Dimers

Two types of scFv-based chimeric molecules were constructed to assess the ability of scFv-based molecules to activate the rTie-1 receptor. One type of molecule used a single scFv fused to both the N-terminus and the C-terminus of hFc, the consequence of which was a monospecific tetravalent molecule capable of binding rTie-1. This molecule should be capable of simultaneously binding four rTie-1 molecules. The plasmid pTE778 encodes the gene for $scFv_{1-1F11}$-FC-$scFv_{1-1F11}$ (SEQ ID NO:50) and contains the mROR1 signal peptide and CMV-MIE promoter. The protein was expressed and purified as described above.

Construction of an scFv-Fc-scFv molecule where the two scFv domains are derived from two different non-competing anti-rTie-1 antibodies is expected to yield a molecule capable of clustering more than four receptors, in contrast to the $scFv_{1-1F11}$-Fc-$scFv_{1-1F11}$ described above, which can cluster only four receptors. It was determined by BlAcore analysis that the binding of the 1-1F11 antibody did not block binding of 2-1G3 to rTie-1, and 1-1F11 binding first did not block binding of 2-1G3. Consequently, scFv molecules made from these antibodies should be capable of clustering more than four receptors. To construct a bispecific tetravalent scFv-based molecule, the $scFv_{2-1G3}$ gene was used in combination with the $scFv_{1-1F11}$ gene to yield $scFv_{2-1G3}$-Fc-$scFv_{1-1F11}$ (SEQ ID NO:51). Both constructs were expressed and purified as described above.

The following Tie-binding proteins were also made: a Tie-binding protein that is a dimer of a polypeptide that has an scFv that binds rat Tie-1 linked to a multimerizing component that is an Fc portion, linked to an FD1 ($scFv_{1-1F11}$-Fc-FD1) (SEQ ID NO:52); and a Tie-binding protein that is a dimer of a polypeptide that has an scFv that binds rat Tie-1 linked to a multimerizing component that is an Fc portion, linked to an FD2 ($scFv_{1-1F11}$-Fc-FD2) (SEQ ID NO:53).

Example 9

Activity of Activating Dimers $ScFv_{1-1F11}$-Fc-FD1 was tested for its ability to activate rTie-1 and rTie-2 in a RAEC assay as described herein. Exposure of $scFv_{1-1F11}$-Fc-FD1 to RAECs bearing rTie-1 and rTie-2 resulted in a high degree of phosphorylation of both Tie-1 and Tie-2, as measured by phosphotyrosine blot of immunoprecipitates generated using anti-Tie-1 or anti-Tie-2. Phosphotyrosine blots showed a level of phosphorylation of both Tie-1 and Tie-2 that appeared to be at least double the phosphorylation exhibited by exposing the cells to $scFv_{1-1F11}$-Fc-FD2 and at least 10-fold or more over a mock challenge (i.e., no antibody); in the same assay, a monospecific antibody that binds rTie-1 showed little to no phosphorylation of either Tie-1 or Tie-2.

$ScFv_{1-1F11}$-Fc-FD1 was also compared in a RAEC assay with the following Tie-binding proteins: $scFv_{B2}$-Fc-FD1, $scFv_{B2}$-Fc-FD2, $scFv_{1-1F11}$-Fc-$scFv_{B2}$, $scFv_{1-1F11}$Fc-FD2, and FD1-Fc-FD1. Blots of the Tie-1 phosphorylation assays revealed that $scFv_{1-1F11}$-Fc-FD1 resulted in the highest phosphorylation of Tie-1 for Tie-binding proteins tested and among the highest activation of Tie-2 for the Tie-binding proteins tested.

We claim:

1. A homodimer formed from two fusion polypeptides of the form (A)-M-(A'), wherein component A comprises a single chain variable fragment (scFv) antibody capable of binding Tie-1, component M comprises a multimerizing component comprising an Fc domain of IgG, and component A' comprises i) a fibrinogen domain of Ang1 or Ang2, or ii) a single chain variable fragment (scFv) antibody capable of binding Tie-2, wherein said homodimer binds to both Tie-1 and Tie-2 receptors and clusters four or more Tie receptors of the cell resulting in phosphorylation of both Tie-1 and Tie-2 receptors.

2. A pharmaceutical composition, comprising the homodimer of claim 1 and a pharmaceutically acceptable carrier.

3. The homodimer of claim 1, wherein the scFv antibody capable of binding Tie-2 comprises a HCDR1 of amino acids 58-65 of SEQ ID NO:28, a HCDR2 of amino acids 83-90 of SEQ ID NO:28, a HCDR3 of amino acids 129-139 of SEQ ID NO:28, a LCDR1 of amino acids 192-201 of SEQ ID NO:28, a LCDR2 of amino acids 219-221 of SEQ ID NO:28, and a LCDR3 of amino acids 258-265 of SEQ ID NO:28.

4. The homodimer of claim 1, wherein the scFv antibody capable of binding Tie-2 comprises a HCDR1 of amino acids 58-66 of SEQ ID NO:29, a HCDR2 of amino acids 84-90 of SEQ ID NO:29, a HCDR3 of amino acids 129-143 of SEQ ID NO:29, a LCDR1 of amino acids 196-201 of SEQ ID NO:29, a LCDR2 of amino acids 219-221 of SEQ ID NO:29, and a LCDR3 of amino acids 258-265 of SEQ ID NO:29.

5. The homodimer of claim 1, wherein the scFv antibody capable of binding Tie-2 comprises a HCDR1 of amino acids 58-66 of SEQ ID NO:31, a HCDR2 of amino acids 84-90 of SEQ ID NO:31, a HCDR3 of amino acids 129-137 of SEQ ID NO:31, a LCDR1 of amino acids 196-201 of SEQ ID NO:31, a LCDR2 of amino acids 219-221 of SEQ ID NO:31, and a LCDR3 of amino acids 258-264 of SEQ ID NO:31.

6. The homodimer of claim 1, wherein the fibrinogen domain is selected from the group consisting of amino acids 515-728 of SEQ ID NO:30 and amino acids 515-727 of SEQ ID NO:31.

7. The homodimer of claim 1, wherein the scFv antibody capable of binding Tie-1 comprises a heavy chain variable region of amino acids 4-125 and a light chain variable region of amino acids 141-248 of SEQ ID NO:50.

8. The homodimer of claim 1, wherein the scFv antibody capable of binding Tie-1 comprises a HCDR1 of amino acids 29-36 of SEQ ID NO:50, a HCDR2 of amino acids 54-61 of SEQ ID NO:50, a HCDR3 of amino acids 100-114 of SEQ ID NO:50, a LCDR1 of amino acids 167-172 of SEQ ID NO:50, a LCDR2 of amino acids 190-192 of SEQ ID NO:50, and a LCDR3 of amino acids 229-237 of SEQ ID NO:50.

9. The homodimer of claim 1, wherein the scFv antibody capable of binding Tie-1 comprises a heavy chain variable region of amino acids 4-122 and a light chain variable region of a sequence selected from the group consisting of amino acids 138-244 of SEQ ID NO:51 and amino acids 138-245 of SEQ ID NO:51.

10. The homodimer of claim 1, wherein the scFv antibody capable of binding Tie-1 comprises a HCDR1 of amino acids 29-36 of SEQ ID NO:51, a HCDR2 of amino acids 54-61 of SEQ ID NO:51, a HCDR3 of amino acids 100-111 of SEQ ID NO:51, a LCDR1 of amino acids 164-169 of SEQ ID NO:51, a LCDR2 of amino acids 187-189 of SEQ ID NO:51, and a LCDR3 of amino acids 226-234 of SEQ ID NO:51.

11. A nucleic acid molecule encoding a fusion polypeptide of the form (A)-M-(A'), wherein component A comprises a single chain variable fragment (scFv) antibody capable of binding Tie-1, component M comprises a multimerizing component comprising an Fc domain of IgG, and component A' comprises i) a fibrinogen domain of Ang1 or Ang2, or ii) a single chain variable fragment (scFv) antibody capable of binding Tie-2.

12. A nucleic acid molecule encoding a fusion polypeptide, wherein the fusion polypeptide comprises scFv$_{1-1F11}$-Fc-FD1 (SEQ ID NO: 52).

13. A nucleic acid molecule encoding a fusion polypeptide, wherein the fusion polypeptide comprises scFv scFv$_{1-1F11}$-Fc-FD2 (SEQ ID NO: 53).

14. A homodimer formed from two fusion polypeptides of the form (A)-M-(A'), wherein component A comprises i) a fibrinogen domain of Ang1 or Ang2, or ii) a single chain variable fragment (scFv) antibody capable of binding Tie-2, component M comprises a multimerizing component comprising an Fc domain of IgG, and component A' comprises a single chain variable fragment (scFv) antibody capable of binding Tie-1, wherein said homodimer binds to both Tie-1 and Tie-2 receptors and clusters four or more Tie receptors of the cell resulting in phosphorylation of both Tie-1 and Tie-2 receptors.

15. The homodimer of claim 14, wherein component A comprises a fibrinogen domain of Ang1.

16. The homodimer of claim 14, wherein component A comprises a fibrinogen domain of Ang2.

17. The homodimer of claim 14, wherein component M comprises an Fc domain of human IgG1.

18. A pharmaceutical composition comprising the homodimer of claim 14 and a pharmaceutically acceptable carrier.

19. The homodimer of claim 14, wherein the scFv antibody capable of binding Tie-2 comprises a HCDR1 of amino acids 58-65 of SEQ ID NO:28, a HCDR2 of amino acids 83-90 of SEQ ID NO:28, a HCDR3 of amino acids 129-139 of SEQ ID NO:28, a LCDR1 of amino acids 192-201 of SEQ ID NO:28, a LCDR2 of amino acids 219-221 of SEQ ID NO:28, and a LCDR3 of amino acids 258-265 of SEQ ID NO:28.

20. The homodimer of claim 14, wherein the scFv antibody capable of binding Tie-2 comprises a HCDR1 of amino acids 58-66 of SEQ ID NO:29, a HCDR2 of amino acids 84-90 of SEQ ID NO:29, a HCDR3 of amino acids 129-143 of SEQ ID NO:29, a LCDR1 of amino acids 196-201 of SEQ ID NO:29, a LCDR2 of amino acids 219-221 of SEQ ID NO:29, and a LCDR3 of amino acids 258-265 of SEQ ID NO:29.

21. The homodimer of claim 14, wherein the scFv antibody capable of binding Tie-2 comprises a HCDR1 of amino acids 58-66 of SEQ ID NO:31, a HCDR2 of amino acids 84-90 of SEQ ID NO:31, a HCDR3 of amino acids 129-137 of SEQ ID NO:31, a LCDR1 of amino acids 196-201 of SEQ ID NO:31, a LCDR2 of amino acids 219-221 of SEQ ID NO:31, and a LCDR3 of amino acids 258-264 of SEQ ID NO:31.

22. The homodimer of claim 14, wherein the fibrinogen domain is selected from the group consisting of amino acids 515-728 of SEQ ID NO:30 and amino acids 515-727 of SEQ ID NO:31.

23. The homodimer of claim 14, wherein the scFv antibody capable of binding Tie-1 comprises a heavy chain variable region of amino acids 4-125 and a light chain variable region of amino acids 141-248 of SEQ ID NO:50.

24. The homodimer of claim 14, wherein the scFv antibody capable of binding Tie-1 comprises a HCDR1 of amino acids 29-36 of SEQ ID NO:50, a HCDR2 of amino acids 54-61 of SEQ ID NO:50, a HCDR3 of amino acids 100-114 of SEQ ID NO:50, a LCDR1 of amino acids 167-172 of SEQ ID NO:50, a LCDR2 of amino acids 190-192 of SEQ ID NO:50, and a LCDR3 of amino acids 229-237 of SEQ ID NO:50.

25. The homodimer of claim 14, wherein the scFv antibody capable of binding Tie-1 comprises a heavy chain variable region of amino acids 4-122 and a light chain variable region of a sequence selected from the group consisting of amino acids 138-244 of SEQ ID NO:51 and amino acids 138-245 of SEQ ID NO:51.

26. The homodimer of claim 14, wherein the scFv antibody capable of binding Tie-1 comprises a HCDR1 of amino acids 29-36 of SEQ ID NO:51, a HCDR2 of amino acids 54-61 of SEQ ID NO:51, a HCDR3 of amino acids 100-111 of SEQ ID NO:51, a LCDR1 of amino acids 164-169 of SEQ ID NO:51, a LCDR2 of amino acids 187-189 of SEQ ID NO:51, and a LCDR3 of amino acids 226-234 of SEQ ID NO:51.

27. A nucleic acid molecule encoding a fusion polypeptide of the form (A)-M-(A'), wherein component A comprises i) a fibrinogen domain of Ang1 or Ang2, or ii) a single chain variable fragment (scFv) antibody capable of binding Tie-2, component M comprises a multimerizing component comprising an Fc domain of IgG, and component A' comprises a single chain variable fragment (scFv) antibody capable of binding Tie-1.

\* \* \* \* \*